United States Patent
Kura et al.

(10) Patent No.: US 7,938,772 B2
(45) Date of Patent: May 10, 2011

(54) INSERTION APPARATUS

(75) Inventors: Yasuhito Kura, Hachioji (JP); Takahiro Kishi, Yokohama (JP); Akira Suzuki, Yamanashi (JP); Akira Taniguchi, Hachioji (JP); Katsutaka Adachi, Hino (JP); Makoto Abe, Hachioji (JP)

(73) Assignee: Olympus Corporation, Tokyo (JP)

( * ) Notice: Subject to any disclaimer, the term of this patent is extended or adjusted under 35 U.S.C. 154(b) by 969 days.

(21) Appl. No.: 11/599,549

(22) Filed: Nov. 14, 2006

(65) Prior Publication Data

US 2007/0060790 A1  Mar. 15, 2007

Related U.S. Application Data

(63) Continuation of application No. PCT/JP2005/008918, filed on May 16, 2005.

(30) Foreign Application Priority Data

May 14, 2004 (JP) ................................ 2004-145694

(51) Int. Cl.
*A61B 1/00* (2006.01)
(52) U.S. Cl. ....................................... 600/114; 600/137
(58) Field of Classification Search .................. 600/106, 600/114, 124, 125, 137
See application file for complete search history.

(56) References Cited

U.S. PATENT DOCUMENTS

| 4,329,980 A | * | 5/1982 | Terada | 600/144 |
| 4,784,980 A | * | 11/1988 | Bertolacini et al. | 502/25 |
| 4,998,282 A | * | 3/1991 | Shishido et al. | 381/77 |
| 5,301,061 A | * | 4/1994 | Nakada et al. | 359/362 |
| 5,556,367 A | * | 9/1996 | Yabe et al. | 600/124 |
| 5,695,448 A | * | 12/1997 | Kimura et al. | 600/121 |
| 6,478,731 B2 | * | 11/2002 | Speier et al. | 600/125 |
| 7,048,717 B1 | * | 5/2006 | Frassica | 604/165.04 |

FOREIGN PATENT DOCUMENTS

| JP | 54-78883 | 6/1979 |
| JP | 55-42657 | 3/1980 |
| JP | 3-97431 | 4/1991 |
| JP | 6-254034 | 9/1994 |
| JP | 6-304118 | 11/1994 |
| JP | 10-113396 | 5/1998 |
| JP | 10-155733 | 6/1998 |
| JP | 2004-008822 | 1/2004 |

* cited by examiner

*Primary Examiner* — Linda C Dvorak
*Assistant Examiner* — Alireza Nia
(74) *Attorney, Agent, or Firm* — Scully, Scott, Murphy & Presser, P.C.

(57) ABSTRACT

An insertion apparatus includes: an introducing duct including; insertion portion cover portion for covering an insertion portion extending from a distal side portion of a handling portion constituting an endoscope; and a spiral duct which is disposed on an inner circumferential surface side of the insertion portion cover portion, and has on a circumferential surface of the spiral duct, a propulsion power generating portion for applying a propulsion power for introducing the insertion portion into a deep portion in a body cavity, to the insertion portion covered by the insertion portion cover, and a rotating device comprising a rotating portion for rotating the spiral duct equipped to the introducing duct.

21 Claims, 16 Drawing Sheets

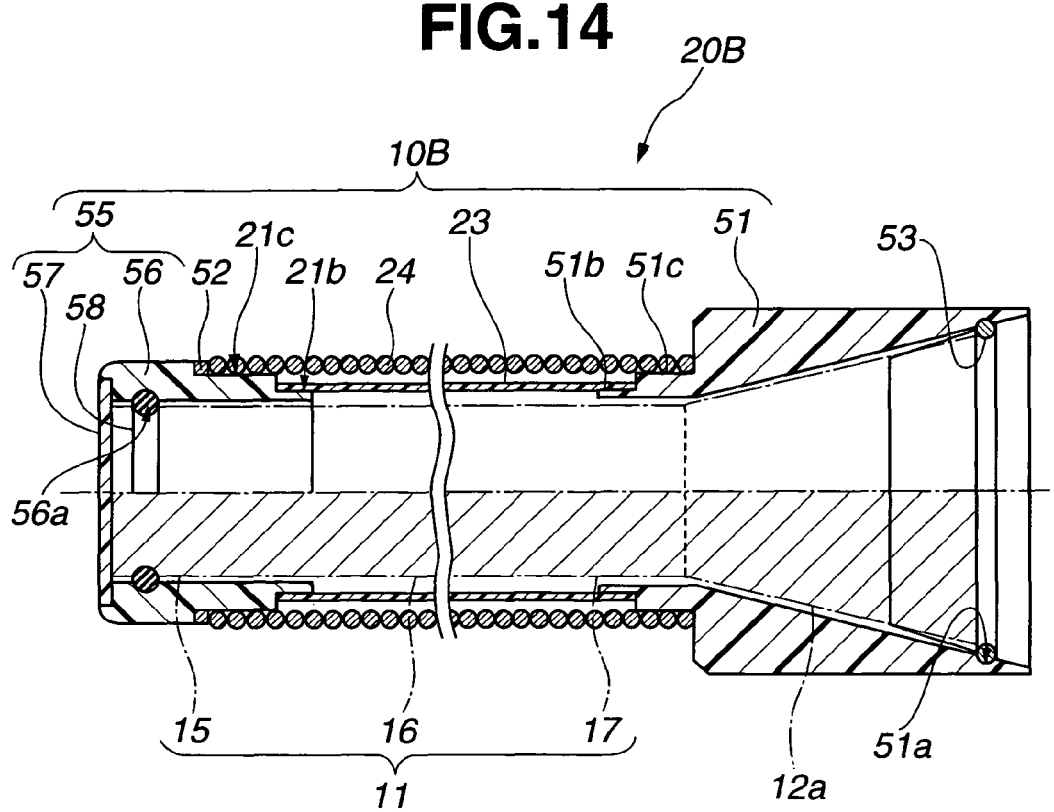
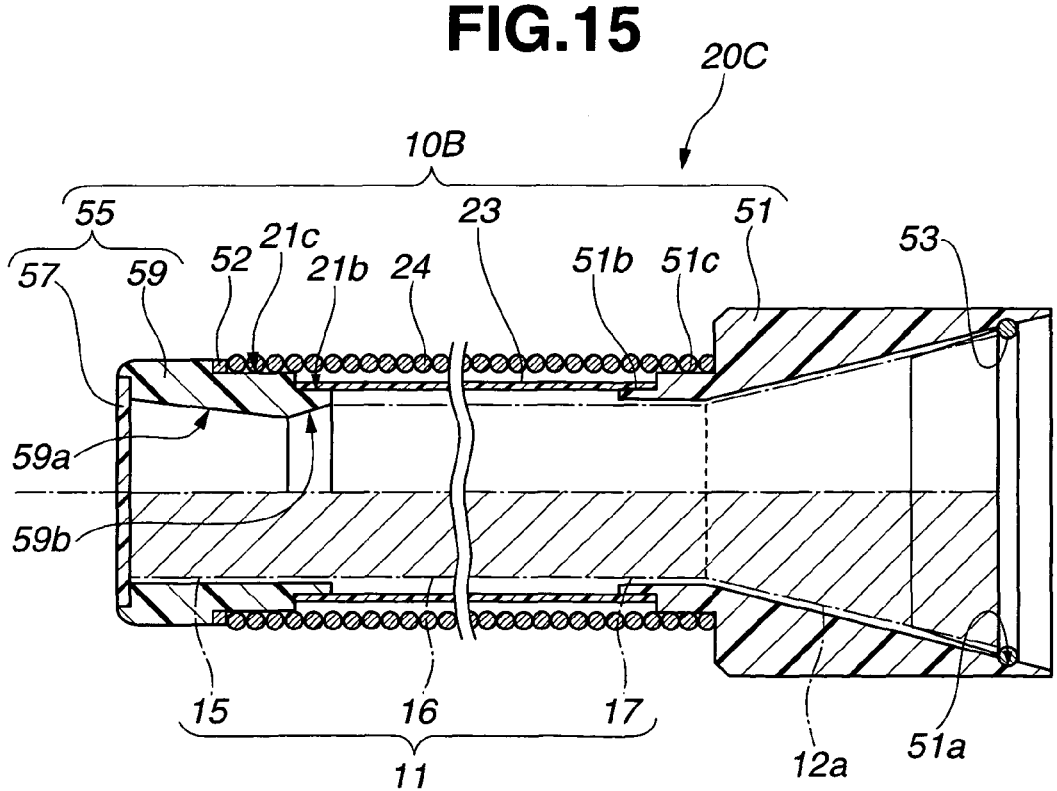

INSERTION APPARATUS

CROSS REFERENCE TO RELATED APPLICATION

This application is a continuation application of PCT/JP2005/008918 filed on May 16, 2005 and claims benefit of Japanese Application No. 2004-145694 filed in Japan on May 14, 2004, the entire contents of which are incorporated herein by this reference.

BACKGROUND OF THE INVENTION

1. Field of the Invention

The present invention relates to an insertion apparatus for generating a propulsion power to introduce an insertion portion into an examinee's body.

2. Description of the Related Art

Recently, an endoscope equipped with an elongated insertion portion having flexibility has been utilized in inspection, treatment, or the like in the medical field. With the endoscope, not only observation of an intracavital organ and the like may be performed without incision by inserting the insertion portion into an intracavital region, but also a variety of therapies and treatments may be performed by introducing an accessory into an intracavital region through a treatment device insertion channel provided in the insertion portion as needed. In the endoscope, a bending section is provided at the distal side of the insertion portion. The bending section can be made to bend in, for example, up and down directions, left and right directions, or the like by performing forward/backward movements of a manipulation wire connected with bending parts constituting the bending section. The manipulation wire is to be moved forward/backward by rotating manipulation of, for example, a bending knob provided at a manipulation section.

When performing endoscopy, the insertion portion must be inserted into an intricately structured intracavital region. When the insertion portion is inserted into a intricately structured lumer, for example, a colon or the like which describes 360 degree loop, an operator manipulates the bending knob to bend the bending section, and performs hand manipulation such as twist manipulation of the insertion portion to move the distal end of the insertion portion toward a target portion to be observed.

However, a skill is required to be able to introduce the insertion portion to the deepest part of the intricately structured colon smoothly in a short time without giving pain to a patient. In other words, there exists a risk that loss of the intended insertion direction may occur when inserting the insertion portion into a deep portion, and a change in shape of the intestine may be caused when inserting the insertion portion into a deep portion of the intestine. Accordingly, various proposals for improving insertability of the insertion portion have been made.

There is disclosed a propulsion device for a medical device which enables easy introduction of the medical device into a deep portion of a live body duct with low invasiblity, for example, in Japanese Patent Application Laid-Open Publication No. H10-113396. In the propulsion device, a rib declining relative to the axial direction of a rotating member is provided at the rotating member. Accordingly, rotating power of the rotating member is converted to propulsion power by the rib by rotation of the rotating member and the medical device connected to the propulsion device is moved in a direction toward the deep portion by the propulsion power.

SUMMARY OF THE INVENTION

An insertion apparatus of the present invention includes: an introducing duct, including; insertion portion cover portion for covering an insertion portion extending from a distal side portion of a handling portion constituting an endoscope; and a spiral duct which is disposed on an inner circumferential surface side of the insertion portion cover portion, and has, on a circumferential surface of the spiral duct, a propulsion power generating portion for applying a propulsion power for introducing the insertion portion into a deep portion in a body cavity, to the insertion portion covered by the insertion portion cover, and a rotating device comprising a rotating portion for rotating the spiral duct equipped to the introducing duct.

BRIEF DESCRIPTION OF THE DRAWINGS

FIG. 14 is a diagram illustrating another exemplary construction of the distal portion body constituting the introducing duct;

FIG. 15 is a diagram illustrating other exemplary construction of the distal portion body constituting the introducing duct;

DESCRIPTION OF THE PREFERRED EMBODIMENTS

Hereinafter, embodiments of the present invention will be described with reference to the drawings.

An embodiment of the present invention will be described with reference to FIG. 1 to FIG. 11.

Figure 1:
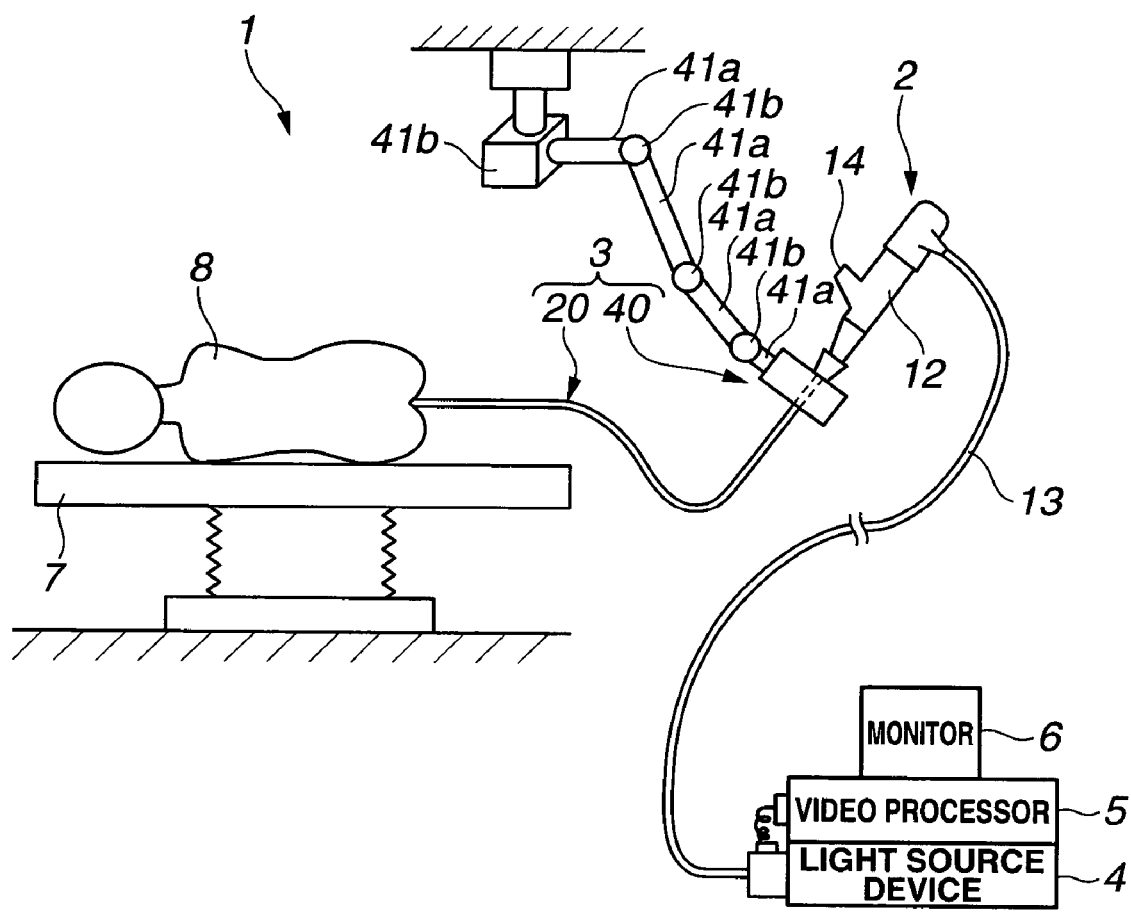
FIG. 1 is a diagram illustrating a construction of an insertion apparatus.

As shown in FIG. 1, an insertion apparatus 1 of the embodiment includes an endoscope 2 and an endoscope insertion ancillary device 3.

The endoscope 2 comprises an insertion portion (see reference numeral 11 in FIG. 2), a handling portion 12 provided at the proximal side of the insertion portion 11, and an universal cord 13 extending from a side portion of the handling portion 12. An accessory inlet 14 and the like are provided at a distal side portion of the handling portion 12 of the endoscope 2. The accessory inlet 14 communicates with an accessory insertion channel (not shown) for introducing an accessory into an intracavital region.

For the endoscope 2, a light source device 4, a video processor 5, and a monitor 6 are provided as external devices. The light source device 4 provides illumination light to the endoscope 2. The video processor 5 includes a controlling circuit for carrying out various controlling operations, a signal processing circuit, and the like. The video processor 5 provides a driving signal for driving an image pick up device (not shown) provided in the endoscope 2 and generates an image signal from an electric signal photoelectrically converted in the image pickup device and transmitted therefrom to output to the monitor 6. On the image screen of the monitor 6, an endoscope image is displayed by receiving the image signal output from the video processor 5.

The endoscope insertion ancillary device 3 includes an introducing duct 20 and a rotating device 40.

Figure 2:
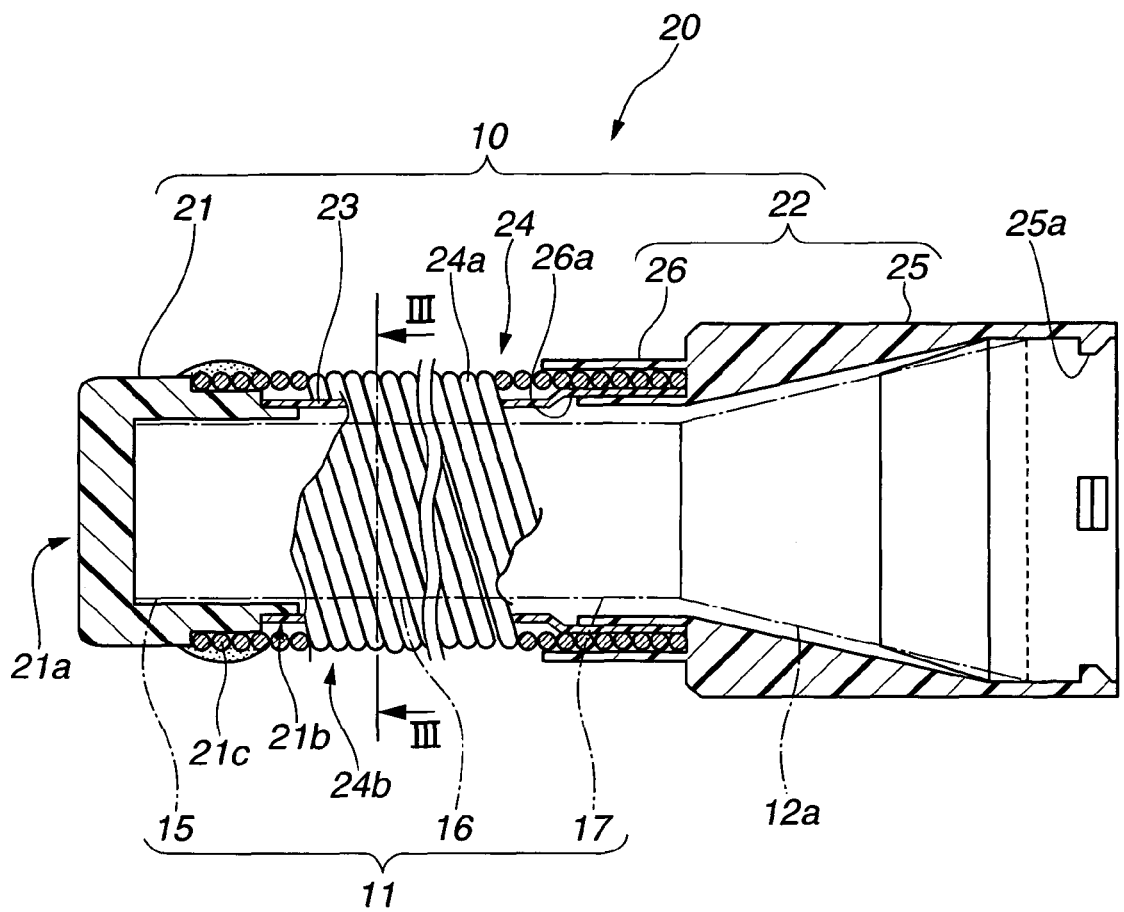
FIG. 2 is a diagram illustrating a construction of an introducing duct including a partial cross-section diagram.
Figure 3:
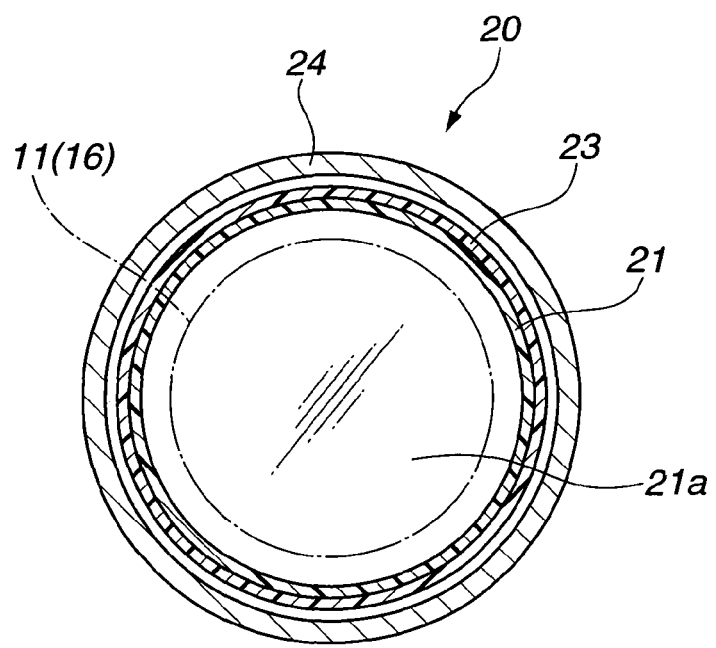
FIG. 3 is a cross-section diagram taken on line III-III of FIG. 2.

As shown in FIGS. 2 and 3, the introducing duct 20 comprises a distal portion body 21 and a proximal portion body 22, a cover member 23, and a spiral duct 24. The distal portion body 21, the proximal portion body 22, and the cover member 23 constitute an insertion portion cover 10 as insertion portion covering means. The spiral duct 24 is a member for generating propulsion power as described below.

The spiral duct 24 is formed in a tubular shape by coiling a metal wire 24a having a predetermined diameter made of, for example, stainless in spiral state to have a predetermined flexibility. Therefore, a spiral portion 24b which is a propulsion power generating portion formed by the surface of the metal wire 24a is provided on the outer surface of the spiral duct 24.

The cover member 23 constituting the insertion portion cover 10 is formed by an elongated tube of flexible resin having a small frictional resistance, for example, Teflon™. The distal portion body 21 constituting the insertion portion cover 10 is cylindrical. Moreover, the distal portion body 21 is formed of a transparent resin member having an optical property, for example, polycarbonate. The distal face of the distal portion body 21 is constituted by a closing window portion 21a. In the distal portion body 21, a distal portion 15 constituting the insertion portion 11 of the endoscope 2 is disposed covered by the distal portion body 21. The inner diameter of the distal portion body 21 is larger than the outer diameter of the distal portion 15 so that a predetermined space is formed between the inner circumferential surface of the distal portion body 21 and the outer circumferential surface of the distal portion 15.

A first shoulder 21b and a second shoulder 21c are formed in this order from the proximal side on the outer circumferential surface of the proximal portion side which is an aperture side of the distal portion body 21. One end of the cover member 23 is coated to be disposed in a water-tight manner by, for example, adhesion at the first shoulder 21b. One end of the spiral duct 24 is integrally fixed by adhesion or the like at the second shoulder 21c. That is, one end of the cover member 23 and one end of the spiral duct 24 are respectively integrally fixed at the corresponding first shoulder 21b and second shoulder 21c in the distal portion body 21.

On the other hand, the proximal portion body 22 constituting the insertion portion cover 10 is tubular. The proximal portion body 22 is formed of a resin member having a good tribological property, such as polyacetal. The proximal portion body 22 includes a rotating fix portion 25 and a connecting fix portion 26. The rotating fix portion 25 is arranged near a break stop (see reference numeral 12a in FIG. 2 and FIG. 5) constituting the distal end side of the handling portion 12. Four convex stopping portions 25a, for example, forming an inclined plane are provided at an even interval in the circumferential direction on the proximal side of the inner circumferential surface of the rotating fix portion 25. The connecting fix portion 26 is constituted so that another end of the cover member 23 and another end of the spiral duct 24 are fixed. Specifically, a connecting groove portion 26a is formed in the connecting fix portion 26. Another end of the cover member 23 is coated to be disposed and another end of the spiral duct 24 is disposed in the connecting groove portion 26a. Then, in the arrangement, adhesion bond is applied to another end of the cover member 23 and the spiral duct 24. Thereby, another end of the cover member 23 is integrally fixed to the proximal portion body 22 in a water-tight manner and another end of the spiral duct 24 is integrally fixed to the proximal portion body 22.

Therefore, the insertion portion cover 10 in which the cover member 23 is fixed to the distal portion body 21 and the proximal portion body 22 in a water-tight manner and having an elongated inner space is constituted. Then, the distal portion 15 of the insertion portion 11 of the endoscope 2 is inserted from the aperture of the proximal portion body 22 into the inner space, and then the distal portion 15 is passed through the cover member 23 to be disposed at the inner circumferential surface side of the distal portion body 21. By doing so, the distal portion 15, a bending section 16, and a flexible duct portion 17 constituting the insertion portion 11 are covered by the insertion portion cover 10.

Note that the spiral duct 24 is not limited to the single strip constitution but may be formed by winding many strips (for example, two strips, four strips, or the like). Besides, when the metal wire 24a is wound in a spiral state, properties of the spiral duct 24 can be variously set by changing the degree of adhesion between portions of the metal wire 24a and by variously changing the angle of the spiral.

Figure 4:
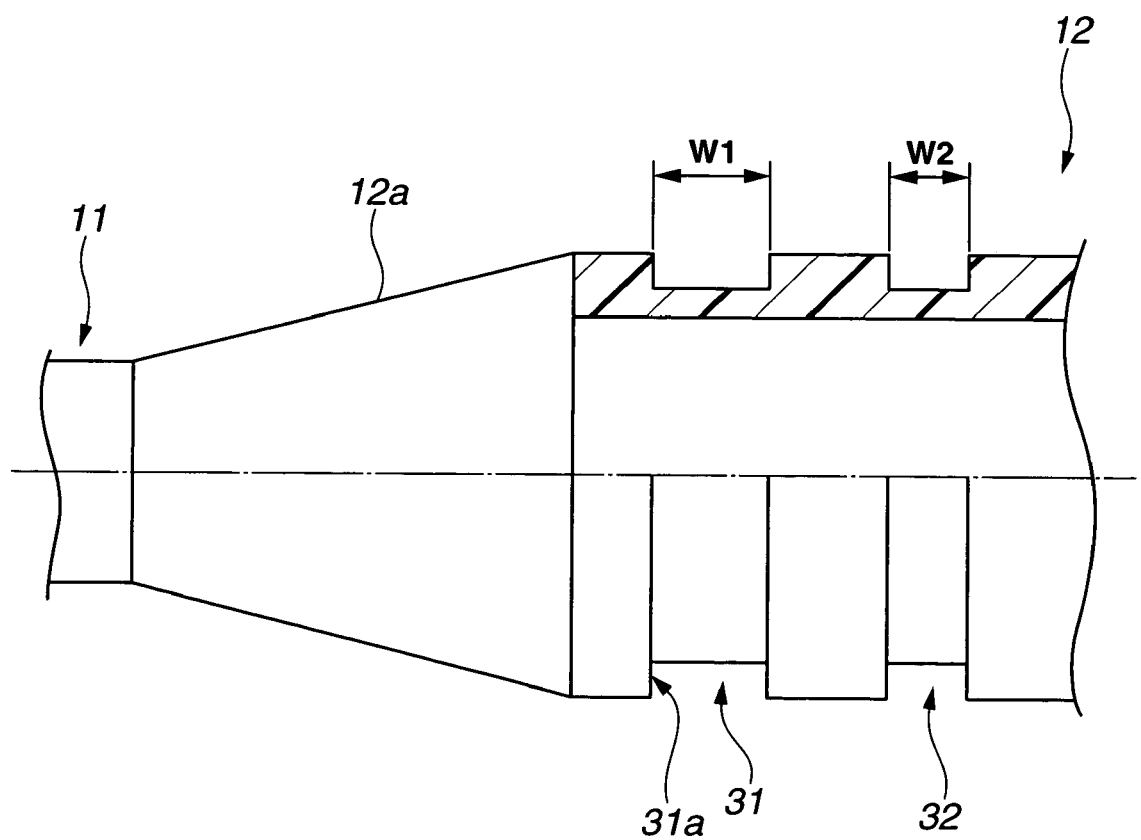
FIG. 4 is a diagram illustrating a construction of a distal side portion of a handling portion in which a proximal portion body constituting the introducing duct is disposed.

As shown in FIG. 4, a circumferential groove portion (hereinafter, abbreviated as circumferential groove) 31 and a stop groove 32 to be stopping portion are provided in this order from the insertion portion 11 side at the distal side portion of the handling portion 12. The convex stopping portions 25a formed on the inner circumferential surface of the rotating fix portion 25 are freely disposed in the circumferential groove 31. The convex stopping portions 25a are engageably inserted to be arranged at the stop groove 32.

The width W1 of the circumferential groove 31 is formed larger than the width of the convex stopping portions 25a so that the convex stopping portion 25a can be rotationally moved smoothly along the circumferential groove 31. On the other hand, the width W2 of the stop groove 32 is formed to be the same as the width of the convex stopping portions 25a and is formed at a predetermined position.

Figure 5:
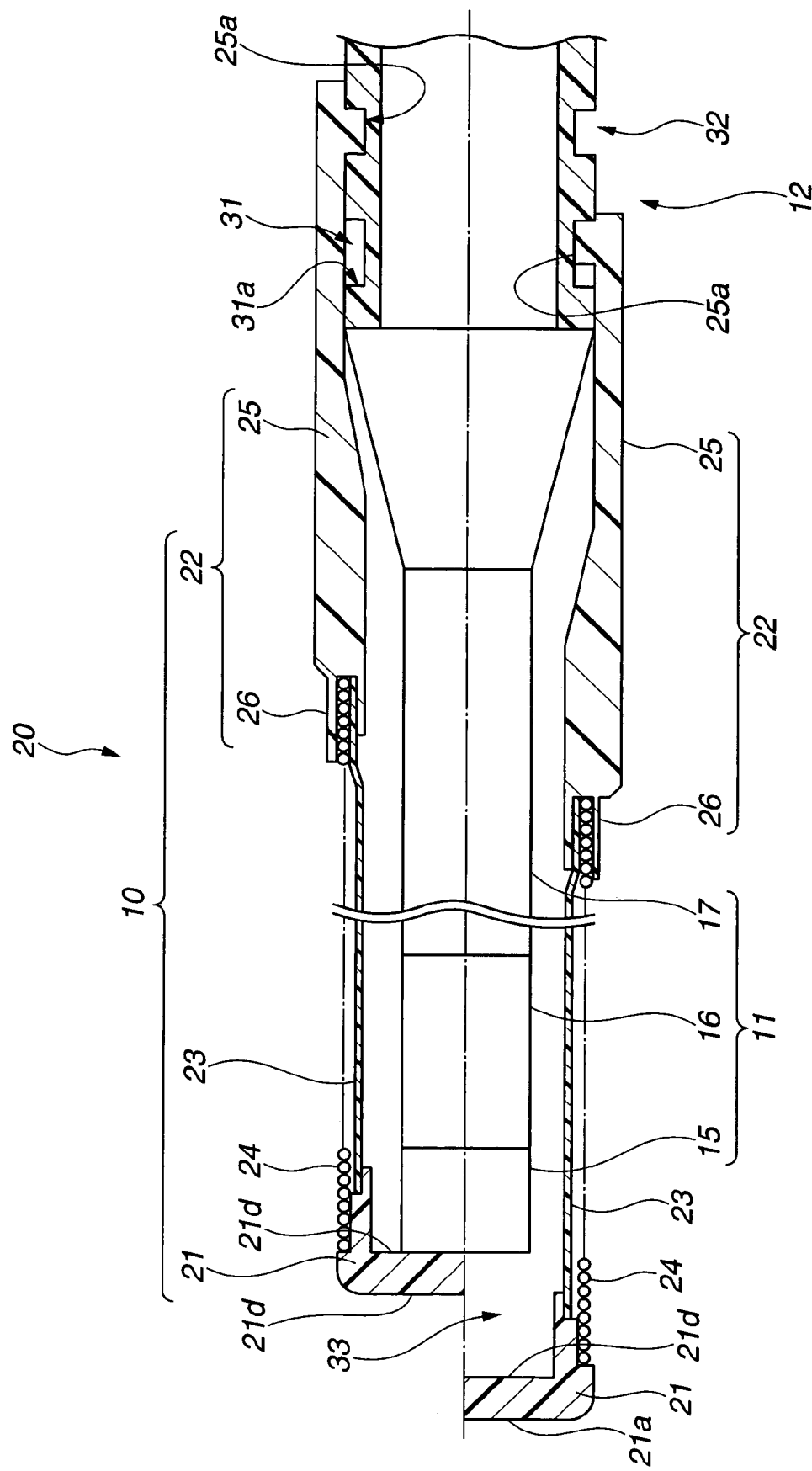
FIG. 5 is a diagram illustrating a relation between the introducing duct and an endoscope inserted into an insertion portion cover of the introducing duct.

Therefore, the convex stopping portions 25a formed at the rotating fix portion 25 are disposed at the circumferential groove 31 under the state where the insertion portion 11 of the endoscope 2 is disposed in the inner space of the insertion portion cover 10 constituting the introducing duct 20 as shown in the lower half of the drawing of FIG. 5. Consequently, a space 33 is formed between the back surface 21d of the closing window portion 21a and the distal surface of the distal portion 15. On the other hand, the convex stopping portions 25a are engageably inserted to be disposed at the stop groove 32 under the state where the insertion portion 11 of the endoscope 2 is disposed in the inner space of the insertion portion cover 10 as shown in the upper half of the drawing of FIG. 5. Consequently, the distal portion body 21 is moved to the distal end side of the distal portion 15 into a predetermined state where the back surface of the closing window portion 21a is adhered with the distal surface of the distal portion 15. Thereby, observation by the endoscope may favorably be performed through the closing window portion 21a in the endoscope 2.

On the other hand, a rotating device 40 constituting the endoscope insertion ancillary device 3 includes, for example, an arm portion 41 and a rotating mechanism portion 42. One end of the arm portion 41 is placed at the seal of an inspecting room. The arm portion 41 includes a plurality of arm members 41a, for example, having different lengths, and joint portions 41b for connecting adjacent arm members 41a in a rotatable manner. The rotating mechanism portion 42 is placed at another end of the arm portion 41. Thereby, the rotating mechanism portion 42 may be moved to any position with a slight force.

Figure 6:
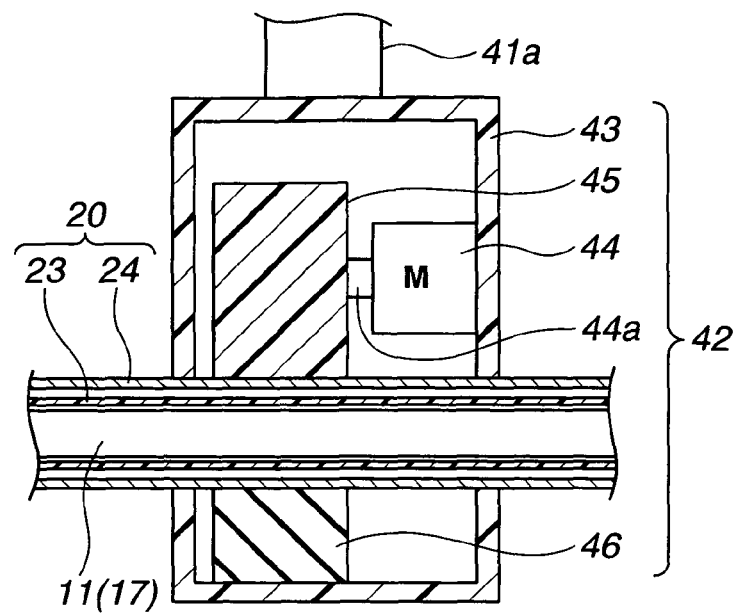
FIG. 6 is a diagram illustrating a construction of a rotating mechanism portion.
Figure 7:
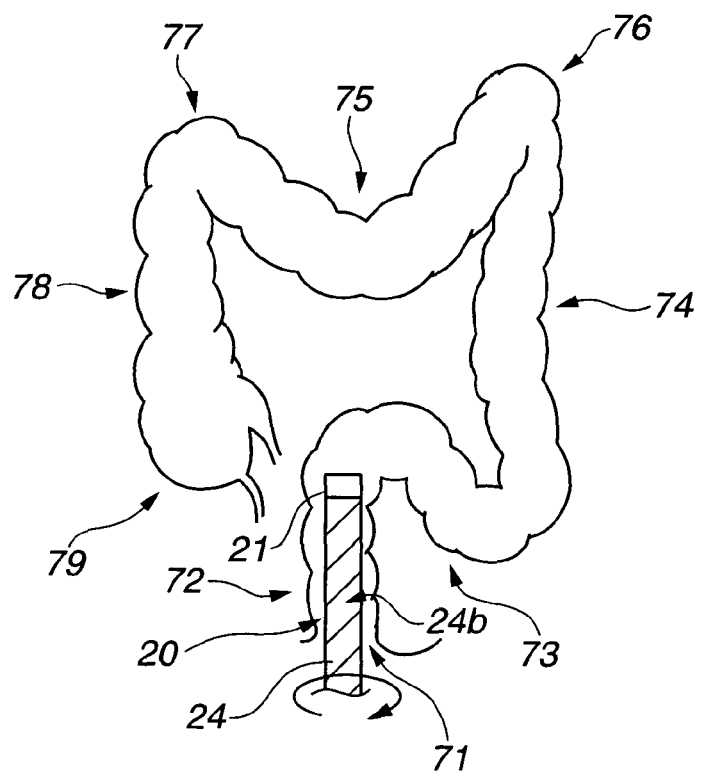
FIG. 7 is a diagram showing a state where the introducing duct in which an insertion portion of the endoscope is inserted to be disposed is inserted from the anus.

As shown in FIG. 6, the rotating mechanism portion 42 includes a rotating portion body 43, a motor 44, a rotating power transmission member 45 which is a rotating portion, and a guidance duct holding portion 46. The motor 44 generates the driving power for rotating the spiral duct 24 in the predetermined direction of the spiral duct longitudinal axis rotation (hereinafter, abbreviated as axis rotation). The motor 44 is fixedly provided at, for example, a side wall of the rotating portion body 43.

The rotating power transmission member 45 is integrally fixed to the motor axis 44a of the motor 44. The rotating power transmission member 45 is formed by a resin member, a rubber member, or the like having elasticity. The guidance duct holding portion 46 is disposed at the position opposing the rotating power transmission member 45 fixed to the motor axis 44a. The guidance duct holding portion 46 is fixed, for example, at the bottom of the rotating portion body 43. A curved surface or a concave portion of hemispherical shape (not shown) which approximately matches the outline shape of the spiral duct 24 or the proximal portion body 22 is formed on the surface portion of the guidance duct holding portion 46 opposing the rotating power transmission member 45. The spiral duct 24 constituting the introducing duct 20 is to be disposed between the rotating power transmission member 45 and the concave portion of the guidance duct holding portion 46 as shown in the drawing.

In the state where convex stopping portions 25a are disposed at the circumferential groove 31 as shown in FIG. 5, the spiral duct 24 constituting the introducing duct 20 in which the insertion portion 11 of the endoscope 2 is disposed is to be disposed between the rotating power transmission member 45 and the guidance duct holding portion 46. Then, the motor 44 is driven. Consequently, the rotating power transmission member 45 integrally fixed to the motor axis 44a is rotated, and the rotation force is transmitted to the spiral duct 24. Here, the introducing duct 20 is smoothly rotated relative to the axis rotation with respect to the insertion portion 11 of the endoscope 2 by respectively integrally fixing both end portions of the spiral duct 24 to the distal portion body 21 and the proximal portion body 22, by integrally providing the cover member 23 to the bodies 21 and 22, and by providing the space 33 between the back surface 21d of the closing window portion 21a and the distal surface of the of the distal portion 15.

An operation of the insertion device 1 constructed as described above will be described.

First, a medical personnel (abbreviated as staff) prepares the endoscope 2 and the introducing duct 20 constituting and the endoscope insertion ancillary device 3. Moreover, the rotating mechanism portion 42 is disposed at the predetermined position by moving the arm portion 41 of the rotating device 40 constituting the endoscope insertion ancillary device 3.

Next, the desired site, for example, the proximal portion side of the spiral duct 24 constituting the introducing duct 20 is disposed between the guidance duct holding portion 46 and the rotating power transmission member 45 constituting the rotating mechanism portion 42. Thereby the proximal portion side of the introducing duct 20 is held by the rotating mechanism portion 42. Then, the distal portion side of the introducing duct 20 is disposed, for example, on a bed 7.

Next, the insertion portion 11 of the endoscope 2 is inserted into the inner portion of the introducing duct 20 from the aperture of the proximal portion body 22 constituting the introducing duct 20. Then, convex stopping portions 25a provided at the proximal portion body 22 are disposed at the circumferential groove 31. Thereby, the insertion portion 11 of the endoscope 2 is covered by the insertion portion cover 10 provided at the introducing duct 20 and the preparation for introducing the endoscope 2 into the colon is completed. At this time, the space 33 is formed between the proximal surface of the distal portion body 21 and the distal surface of the distal portion 15 as shown in the lower half of the drawing of FIG. 5. Note that the light source device 4, the video processor 5, and the monitor 6 which are peripheral device are also prepared with preparation of the endoscope 2, the introducing duct 20, and the rotating device 40.

A procedure for inserting the endoscope 2 covered by the introducing duct 20 into the colon will be described.

At first, an operator (not shown) holds the distal side of the introducing duct 20. Then, the distal portion of the introducing duct 20 is inserted into the anus of the patient 8 lying on the bed 7. Consequently, the spiral portion 24b formed on the outer surface of the spiral duct 24 provided at the introducing duct 20 is made to contact the bowel wall. At this time, the contact state of the spiral portion 24b and the bowel wall resembles that of male and female screws. Moreover, an endoscope image captured by image pickup device of the endoscope 2 through the closing window portion 21a is displayed on the screen of the monitor 6.

In the state where the spiral portion 24b and the bowel wall are made to contact each other, the motor 44 of the rotating mechanism portion 42 is rotatably driven. Consequently, the rotating power transmission member 45 is rotated to transmit the rotating power to the spiral duct 24 disposed between the rotating power transmission member 45 and the guidance duct holding portion 46 as described above. Thereby, the introducing duct 20 is rotated in the axis rotation direction as shown by the arrow in FIG. 7.

In the rotation state, a force such as that for moving a male screw with respect to a female screw is generated at the contact portion between the spiral portion 24b of the spiral duct 24 constituting the rotated introducing duct 20 and the bowel wall, and a propulsion power for advancing the introducing duct 20 is generated. That is, the introducing duct 20 is deeply advanced into the colon by the propulsion power. Consequently, the convex stopping portions 25a provided at the proximal portion body 22 constituting the introducing duct 20 contact the distal side wall 31a of the circumferential groove 31 and the propulsion power generated at the introducing duct 20 is transmitted to the endoscope 2.

Thereby, the insertion portion 11 of the endoscope 2 can be introduced toward the deep portion of the colon by the propulsion power with the introducing duct held by the operator. Here, the introducing duct 20 in which the insertion portion 11 is disposed is introduced toward the intracavital deep portion by a slight force by performing a hand operation for advancing the introducing duct 20.

Figure 8:
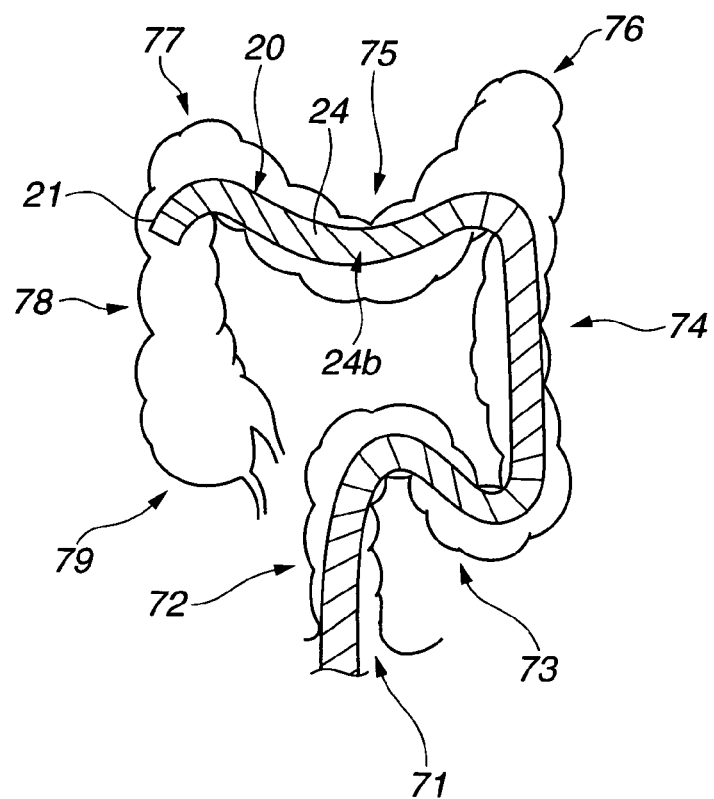
FIG. 8 is a diagram showing a state where a distal portion body of the introducing duct in which the insertion portion of the endoscope is inserted to be disposed is inserted near the cecum portion.

That is, the introducing duct 20 in which the insertion portion 11 of the endoscope 2 is inserted to be disposed inserted from an anus 71 is advanced toward the sigmoid colon 73 from the rectum 72 by the propulsion power and by hand manipulation and bending manipulation and the like performed by the operator. Then, the introducing duct 20 in the rotating state passes through the sigmoid colon 73, and after that, reaches, for example, near the cecum portion 79 which is the observation target portion as shown in FIG. 8 by passing through the bending portion which is the bend between the sigmoid colon 73 and the descending colon 74 which is difficult to move through, the splenic flexure 76 which is the bend between the descending colon 74 and the transverse colon 75 which is easy to move through, and the liver curvature 77 which is the bend between the transverse colon 75 and the ascending colon 78.

When the operator judges that the distal portion body 21 of the introducing duct 20 has reached near the cecum portion 79 from the endoscope image displayed on the screen of the monitor 6, the driving of the motor 44 is stopped by, for example, instruction to the staff. Then, convex stopping portions 25a are engageably inserted to be disposed from the circumferential groove 31 to the stop groove 32 by moving the proximal portion body 22. Thereby, the back surface 21d of the closing window portion 21a enters an adherent state with the distal surface of the distal portion 15, and a good-quality endoscope image desired by the operator is displayed on the screen of the monitor 6. Here, the operator draws back the insertion portion 11 to perform endoscope inspection in the colon.

Then, after finishing the inspection, the insertion portion 11 of the endoscope 2 is withdrawn from the introducing duct 20 and the introducing duct 20 is discarded whereas the insertion portion 11 of the endoscope 2 is inserted into a new introducing duct 20 not yet used. This makes it possible to carry out the next inspection without the need for cleaning and disinfection of the endoscope 2.

In this manner, the introducing duct is constituted by integrally fixing end portions of the spiral duct and the cover member to the distal portion body and proximal portion body, and the stop convex portions provided at the proximal portion body of the introducing duct are freely disposed at the circumferential groove provided at the handling portion of the endoscope. Then, the rotating power of the rotating power transmission member rotated by the motor provided at the rotating mechanism portion is transmitted to the spiral duct to rotate the introducing duct. Consequently, the propulsion power for introducing the introducing duct toward the deep portion of the colon can be obtained, and the introducing duct is moved by the propulsion power. At this time, the propulsion power generated at the introducing duct is transmitted to the endoscope as the convex stopping portions contact the distal side wall of the circumferential groove, so that the insertion portion of the endoscope can be introduced toward the deep portion of the colon by the propulsion power generated at the spiral duct constituting the introducing duct.

Further, end portions of the cover member disposed at the inner circumferential surface side of the spiral duct provided at the introducing duct are adherently disposed to the distal portion body and the proximal portion body in a water-tight manner to constitute the insertion portion cover. Thereby, insertion portion can surely be prevented from directly contacting body walls and the like during inspection by inserting and disposing the insertion portion of the endoscope into the insertion portion cover provided at the insertion tube.

Therefore, after finishing the inspection, the insertion portion of the endoscope is withdrawn from the introducing duct and the introducing duct is discarded whereas the withdrawn endoscope is combined with a new introducing duct to be reused without implementing cleaning and disinfection, so that the staff is relieved from troublesome cleaning and disinfection of the endoscope and the introducing duct at the end of inspection.

Note that in the embodiment, a colon is described as an example of a lumen in which the insertion portion 11 of the endoscope 2 covered with the introducing duct 20 is inserted. However, a lumen to which the insertion portion 11 is inserted is not limited to a colon and may be a lumen and the like such as from an oral cavity, an esophagus, a stomach, to a small bowel and the like.

In addition, a rotating direction of the introducing duct 20 in the embodiment may be only one direction which is an advancing direction, but the rotating direction may be switched between the advancing direction and retreating direction at a constant cycle or random timing. In this manner, by combining the rotations performed in the advancing and the retreating operations, in the event that the distal end of the introducing duct 20 becomes stuck in a small concave section or the like of a wall of the bowel when advancing, it can be released by performing a retreating operation. Then, when advancing again, the introducing duct is smoothly advanced without becoming stuck again because the portions of the bowel and the introducing duct 20 are delicately shifted.

Figure 9:
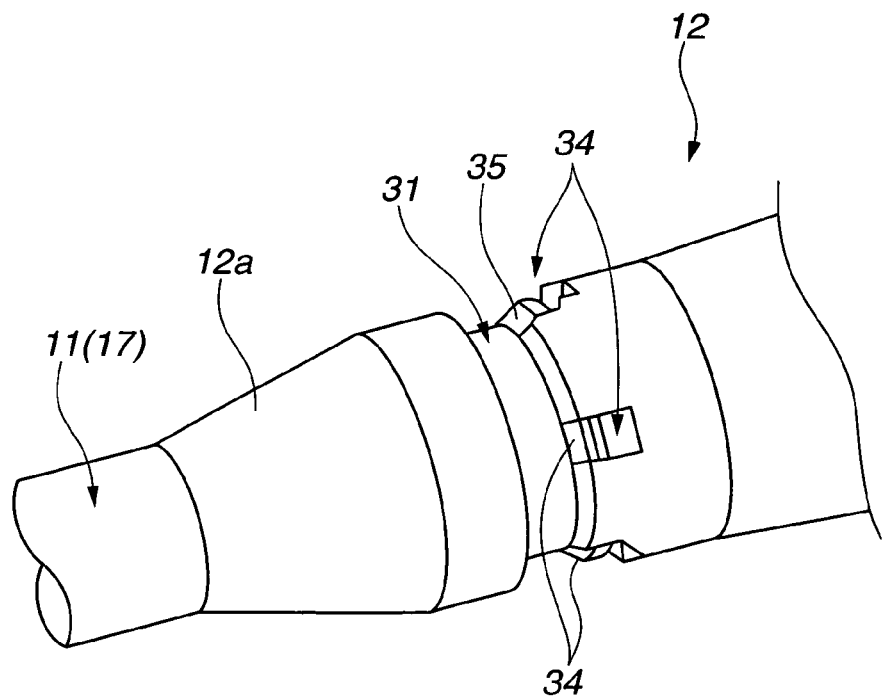
FIG. 9 is a perspective view illustrating another exemplary construction of the distal side portion of the handling portion.
Figure 10:
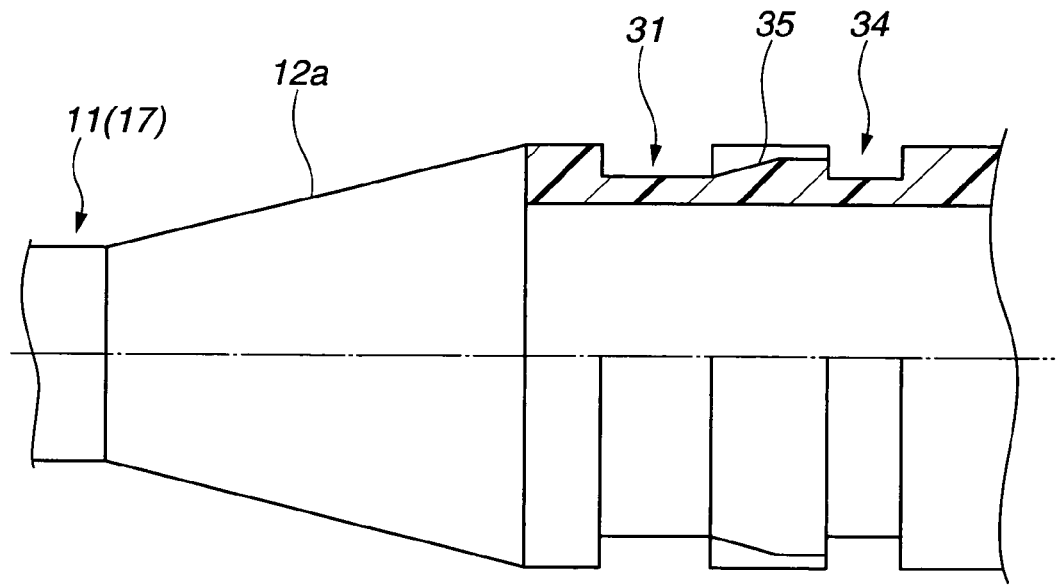
FIG. 10 is a side view of the distal side portion of the handling portion and a partial cross-section diagram thereof shown in FIG. 9.

Further, the stopping portion may be constituted by concave stopping portions 34 as shown in FIG. 9 instead of forming the stop groove 32. Thereby, the proximal portion side of the introducing duct 20 may be prevented from moving in the circumferential direction in the state where the proximal surface of the distal portion body 21 contacts the distal surface of the distal portion 15.

When forming the concave stopping portions 34, inclined surfaces 35 are provided whose outer diameter increases toward the concave stopping portions 34 from the circumferential groove 31 between the circumferential groove 31 and the concave stopping portions 34. Thereby, convex stopping portions 25a can be smoothly moved from the circumferential groove 31 to the stop groove 32 with a slight force.

Figure 11:
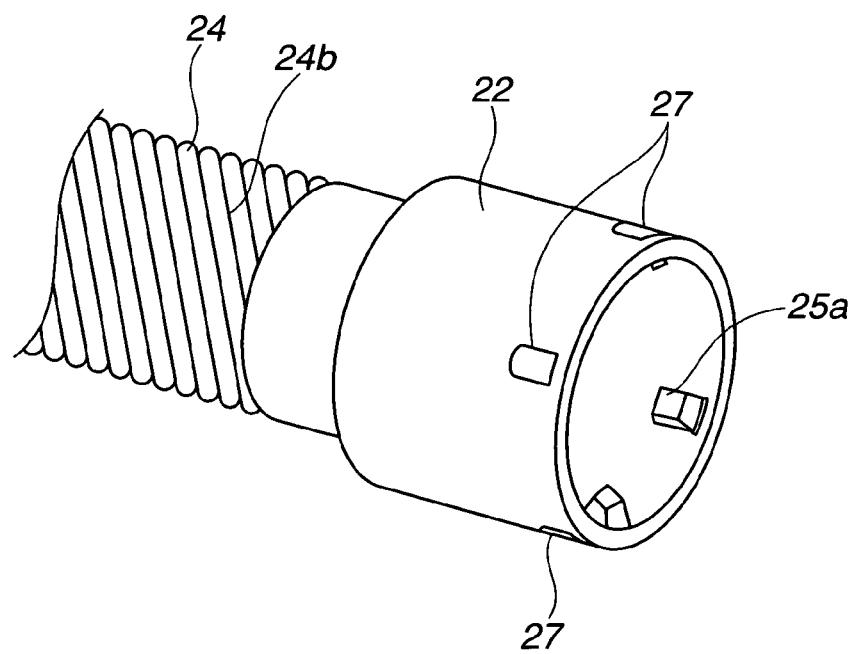
FIG. 11 is a diagram illustrating a proximal portion body provided with eyemarks for informing disposed positions of convex stopping portions.

In addition, eyemarks 27 are provided for informing an operator or a staff of the position of the convex stopping portions 25a at the outer circumferential surface of the proximal portion body 22 constituting the introducing duct 20 as shown in FIG. 11. Thereby, the convex stopping portions 25a can be surely moved from the circumferential groove 31 to the concave stopping portions 34 at one time by carrying out a shifting operation for shifting the proximal portion body 22 to the proximal side in the state where the eyemarks 27 and the concave stopping portion 34 have the same position.

A construction and operation of another construction of the introducing duct having an insertion portion cover will be described with reference to FIG. 12 to FIG. 17.

Figure 12:
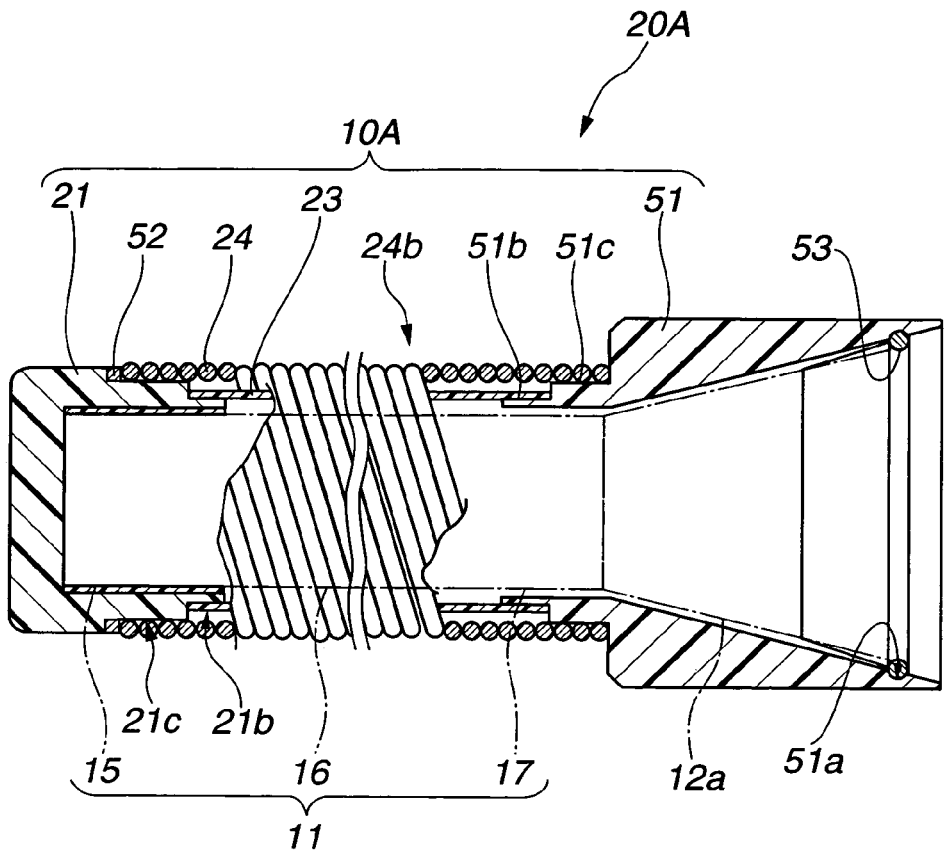
FIG. 12 is a diagram illustrating an introducing duct of another construction.
Figure 13:
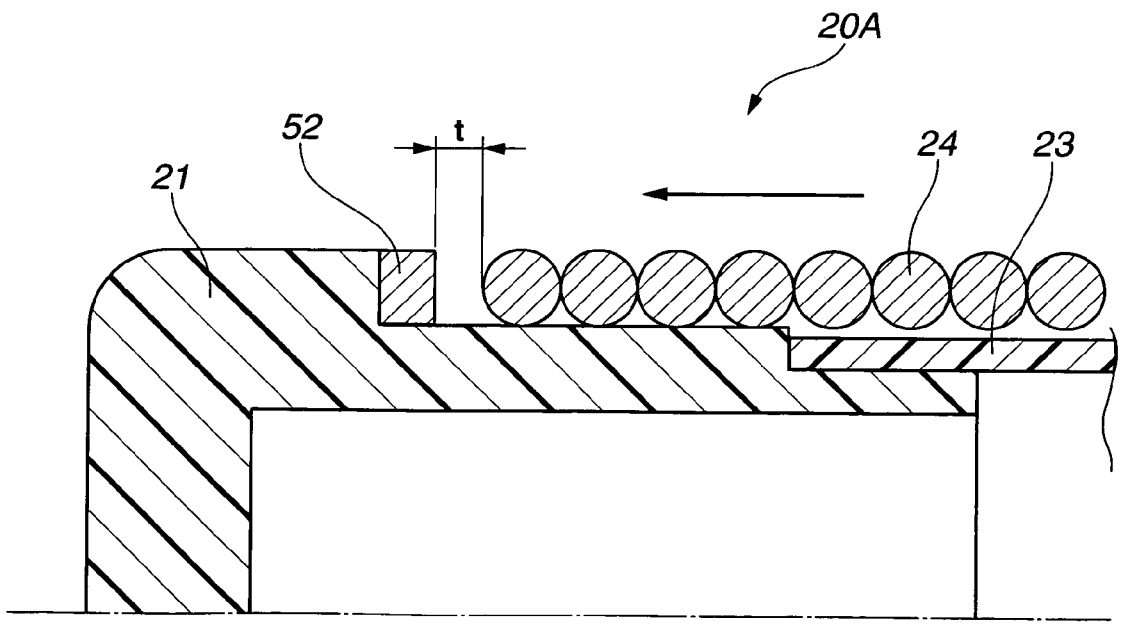
FIG. 13 is an enlarged diagram illustrating a construction near the distal portion of the introducing duct.

As shown in FIG. 12, the introducing duct 20A of the embodiment comprises an insertion portion cover 10A as insertion portion covering means and a spiral duct 24. The insertion portion cover 10A includes a distal portion body 21, a proximal portion body 22, and a cover member 23, and the spiral duct 24 is disposed in a rotatable manner with respect to the distal portion body 21 and a proximal portion body 51.

The proximal portion body 51 is tubular and is formed by a resin member. An O ring providing circumferential groove 51a in which an O ring 53 is disposed on the proximal side inner circumferential surface of the proximal portion body 51 is formed. The O ring 53 is fix means for integrally fixedly providing the proximal portion body 51 at a predetermined position of a crack stop 12a, and is disposed in a water-tight and adherent manner by a predetermined bias power with respect to the outer circumferential surface of the crack stop 12a.

A first shoulder 51b and a second shoulder 51c are formed in this order from the distal side on the distal side outer circumferential surface of the proximal portion body 51. Another end of the cover member 23 is fixed in a water-tight manner by, for example, adhesion at the first shoulder 51b. Thereby, an insertion portion cover 10A in which the cover member 23 is fixed to the distal portion body 21 and the proximal portion body 51 in a water-tight manner and having an elongated inner space is constituted.

A circular member 52 is a hard member, for example, stainless-steel and is formed to have a predetermined thickness. The circular member 52 is integrally fixedly provided by, for example, adhesion so as to be attached firmly to the wall surface formed at the second shoulder 21c of the distal portion body 21.

Each end portion of the spiral duct 24 of the embodiment is disposed at the second shoulder 21c of the distal portion body 21 and at the second shoulder 51c of the proximal portion body 51 in a rotatable manner. Consequently, in the embodiment, the spiral duct 24 constituting the introducing duct 20A is constituted to rotate with respect to the distal portion body 21 and the proximal portion body 51 in place of the rotation of the introducing duct 20.

In addition, in the spiral duct 24 of the embodiment, for example, a space t having a predetermined size is formed at least between one end surface of the spiral duct 24 and the end surface of the circular member 52 fixedly provided at the second shoulder 21c of the distal portion body 21 or between another end surface of the spiral duct 24 and the wall surface formed at the second shoulder 51c of the proximal portion body 51.

The other constructions are the same as in the embodiment describe above, so that the same reference numerals are applied to the same members to skip the description.

An operation of the insertion apparatus 1 equipped with the introducing duct 20A constructed as described above will be described.

First, a staff prepares an endoscope 2 and an introducing duct 20A and disposing a rotating mechanism portion 42 at a desired position by moving the arm portion 41 of the rotating device 40.

Next, a desired portion, for example, the proximal portion side of the spiral duct 24 constituting the introducing duct 20A is disposed between the guidance duct holding portion 46 and the rotating power transmission member 45 constituting the rotating mechanism portion 42. Thereby, the proximal portion side of the introducing duct 20A is held by the rotating mechanism portion 42.

Then, the insertion portion 11 of the endoscope 2 is inserted into the introducing duct 20 from the aperture of the proximal portion body 51 constituting the introducing duct 20A. Then, the O ring 53 provided at the proximal portion body 51 is attached firmly to the crack stop 12a provided at the endoscope 2 and a water-tight state is held.

Thereby, the proximal portion body 51 is integrally fixed to the proximal portion body 51 by the bias power of the O ring 53. In the fixedly provided state, the insertion portion 11 of the endoscope 2 is covered by the insertion portion cover 10A provided at the introducing duct 20A and the preparation for introducing the endoscope 2 into, for example, a colon is finished. At this time, the proximal surface of the distal portion body 21 and the distal surface of the distal portion 15 is attached firmly as shown in upper half portion of the drawing of FIG. 5. Note that a light source device 4, a video processor 5, and a monitor 6 which are peripheral device are also prepared with preparation of the endoscope 2, the introducing duct 20, and the rotating device 40.

Here, a procedure for inserting the endoscope 2 covered by the introducing duct 20A into a colon will be described.

First, an operator (not shown) holds the distal side of the introducing duct 20A. Then, the distal portion of the introducing duct 20A is inserted into the anus of the patient 8 lying on the bed 7. Consequently, the spiral portion 24b formed on the outer surface the spiral duct 24 provided at the introducing duct 20 is made to contact the bowel wall. At this time, the contact state of the spiral portion 24b and the bowel wall resembles that of male and female screws. Moreover, a good-quality endoscope image captured by image pickup device of the endoscope 2 through the closing window portion 21a is displayed on the screen of the monitor 6.

In the state where the spiral portion 24b and the bowel wall are made to contact each other, the motor 44 of the rotating mechanism portion 42 is rotatably driven. Consequently, the rotating power transmission member 45 is rotated to transmit the rotating power to the spiral duct 24 disposed between the rotating power transmission member 45 and the guidance duct holding portion 46. Thereby, only the spiral duct 24 constituting the introducing duct 20 is rotated around the axis as shown by the arrow in the FIG. 7. Consequently, the propulsion power is generated at the contact portion between the spiral portion 24b of the rotated spiral duct 24 and bowel wall. Thereby, the spiral duct 24 is moved toward the direction of the circular member 52 as shown in the arrow in FIG. 13.

Then, the propulsion power generated at the spiral duct 24 is transmitted to the introducing duct 20A through the distal portion body 21 by the contact of the distal end of the spiral duct 24 and the circular member 52, and the introducing duct 20A is moved into the intracavital deep portion by the propulsion power. In this state, as the introducing duct 20A is integrally provided with respect to the insertion portion 11 of the endoscope 2, the insertion portion 11 is also introduced toward the deep portion with the introducing duct 20A moved toward the intracavital deep portion by the propulsion power. Therefore, the introducing duct 20A in which the insertion portion 11 of the endoscope 2 is integrally disposed is introduced toward the intracavital deep portion by a slight force by performing a hand operation for advancing the introducing duct 20A by the operator.

In this manner, each end portion of the spiral duct 24 constituting the introducing duct integrally provided with respect to the insertion portion of the endoscope is provided in a rotatable manner at the distal portion body and the proximal portion body. Then, the rotating power of the rotating power transmitting member rotated by the motor provided in the rotating mechanism portion is transmitted to the spiral duct 24. Consequently, the spiral duct becomes a rotating state with respect to the distal portion body and the proximal portion body constituting the introducing duct to be able to obtain the propulsion power for introducing the introducing duct toward the deep portion. Subsequently, the spiral duct in the rotating state moved by the propulsion power contacts the circular member fixedly provided at the distal portion body. Thereby, the propulsion power generated at the spiral duct can be transmitted to the introducing duct through the distal portion body without decrement. The other operation and effect are the same as in the embodiment described above.

Note that the distal portion body 55 may be constituted by a distal member 56 and a closing window member 57 as the introducing duct 20B shown in FIG. 14. The distal member 56 is tubular and a first shoulder 21b and a second shoulder 21c are provided at the outer circumferential surface proximal portion side of the distal member 56. The closing window member 57 is an optical member made of, for example, a resin constituting a closing window and provided at the distal surface of the distal member 56.

Thereby, the distal member 56 can be formed not of a resin member having optical property but commodity type resin member. In this construction, the insertion portion cover 10B is fixed to the distal portion body 55 equipped with the closing window member 57 and the proximal portion body 51 with the cover member 23 in a water-tight manner to constitute an elongated inner space. The other construction and operation/effect are the same as in the embodiment described above.

Further, an O ring providing circumferential groove 56a may be formed on the inner circumferential surface of the distal portion member 56 for the distal portion body 55 to provide an O ring 58 having approximately the same operation as the O ring 53, that is, having a predetermined bias power.

Thereby, the O ring 58 is integrally press-disposed with respect to the outer circumferential surface of the distal portion 15 of the insertion portion 11 provided at the inner portion of the distal portion body 55 by the elastic force. Accordingly, the distal portion body 55 is also fixed with respect to the insertion portion 11 in addition to the proximal portion body 51, so that the introducing duct 20B can more surely integrally be fixed at the insertion portion 11 of the endoscope 2. The other construction and operation/effect are the same as in the embodiment described above.

Further, the distal portion body 55 may be constituted by a distal member 59 and a closing window member 57 as the introducing duct 20C shown in FIG. 15. The distal member 59 also serves as fixing means and is formed in a tubular shape of an elastic member. A first shoulder 21b and a second shoulder 21c are provided at the outer circumferential surface proximal portion side of the distal member 59. The trough-hole of the distal member 59 is constituted by a tapered surface 59a for forming a distal side and a guide surface 59b for forming a proximal side. Inner diameter of the tapered surface 59a is gradually narrowed by a predetermined amount than outer diameter of the distal portion 15 toward from the closing window member 57 side to the proximal side. The inner diameter of the proximal side of the guide surface 59b is somewhat lager than the outer diameter of the distal portion 15 and the inner diameter is gradually narrowed toward the distal side.

Therefore, the distal portion body 55 and insertion portion 11 of the distal portion 15 can be integrally fixed by the elastic force by disposing the distal portion 15 of the insertion portion 11 at a predetermined position against the elastic force of the distal portion body 55. The other construction and operation/effect are the same as in the embodiment described above.

Figure 16:
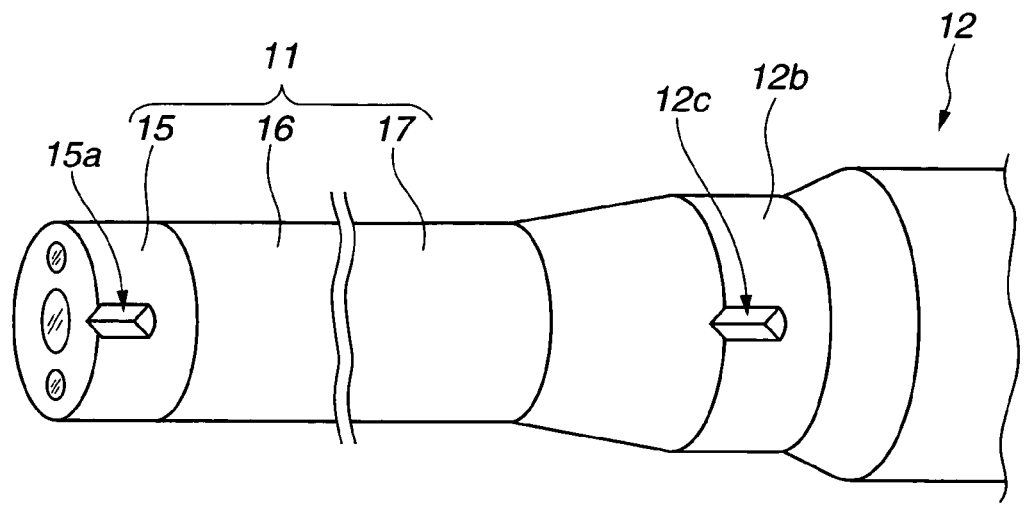
FIG. 16 is a diagram illustrating stop grooves formed at the distal portion of the endoscope and the distal side portion of the handling portion.

Moreover, stopping grooves 15a and 12c for preventing the distal portion body (not shown) and the proximal portion body (not shown) to be displaced or rotated in the circumference direction may be formed at the distal portion 15 of the endoscope 2 and the distal side portion 12b of the handling portion 12 as positional displacement prevention grooves serving as fixing means or displace preventing means as shown in FIG. 16. When forming the stopping grooves 15a and 12c, not shown convex portions engageably inserted to be disposed at the stopping grooves 15a and 12c are respectively provided at the distal portion body and the proximal portion body.

Figure 17:
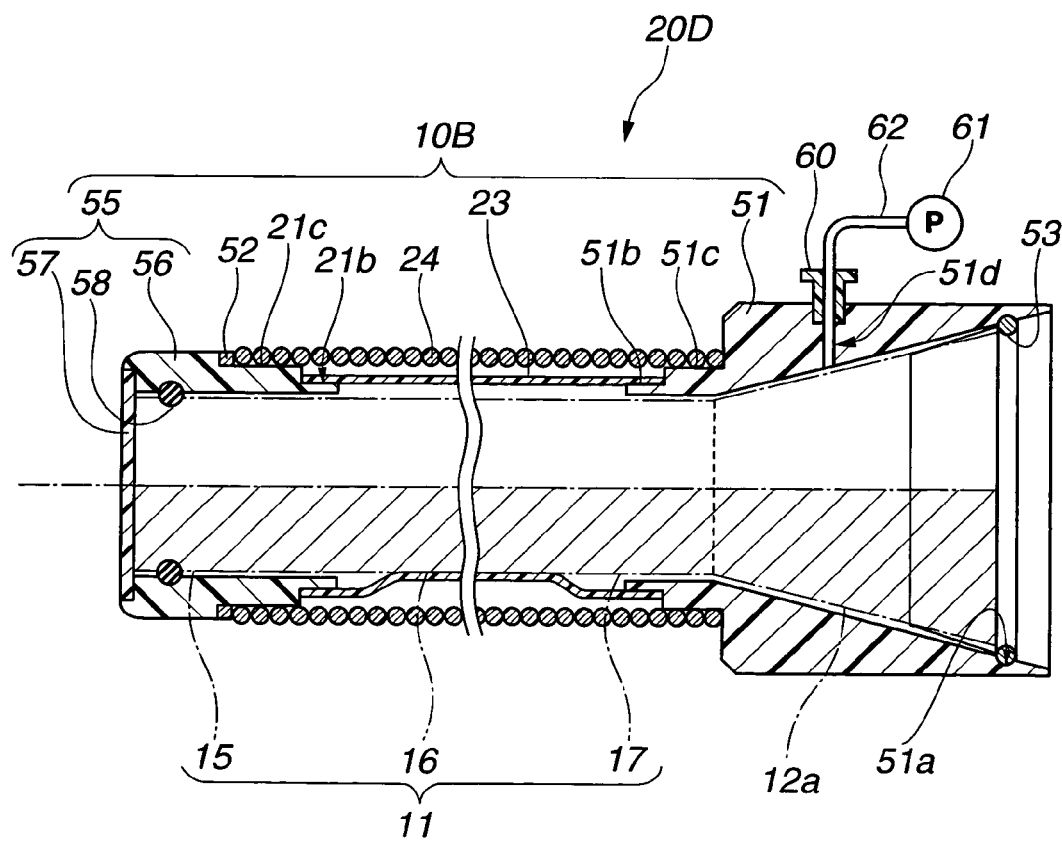
FIG. 17 is a diagram illustrating a construction of the introducing duct in which a cover member is adhered to the insertion portion of the endoscope.

Further, for the introducing duct 20D show in FIG. 17, a continuous hole 51d for communicating the outer portion of the body portion and the inner hole of the body portion is provided at the distal portion body 51 as shown in FIG. 4. A cap portion 60 is provided at the continuous hole 51d, and an aspiration tube 62 extended from an aspiration pump 61 is connected to the cap portion 60.

Then, the air between the insertion portion 11 and the cover member 23 is aspirated by the aspiration pump 61 in the state where the insertion portion 11 of the endoscope 2 is inserted to be disposed in the insertion cover 10B constituting the introducing duct 20D. Consequently, the cover member 23 adheres to the insertion portion 11 of the endoscope 2.

Thereby, the spiral duct 24 rotated by the motor 44 in the rotating mechanism portion 42 is prevented from contacting to the cover member 23 and the occurrence of defects such as a perforation, a tear and the like can be surly prevented. The other construction and operation/effect are the same as in the embodiment described above.

A construction and operation of another construction of the introducing duct having an insertion portion cover will be described with reference to from FIG. 18 to FIG. 23.

Figure 18:
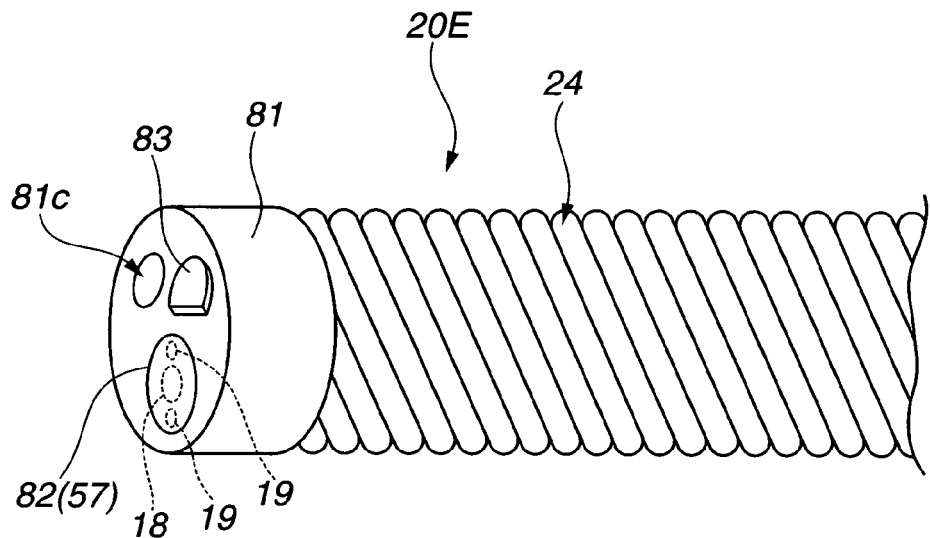
FIG. 18 a perspective view illustrating another construction of the introducing duct.
Figure 19:
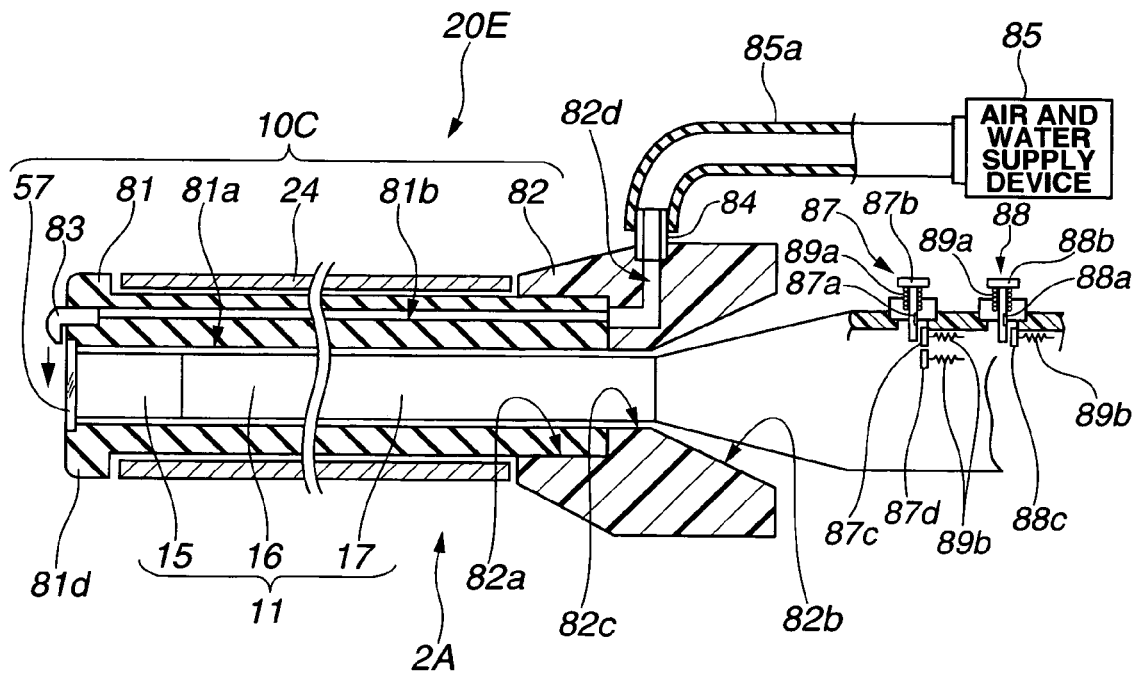
FIG. 19 is a longitudinal direction cross-section diagram illustrating the construction of the introducing duct in FIG. 18.

An insertion portion cover 10C which is insertion portion covering is constituted by an elastic cover tube 81 and a proximal portion constituting member 82 for the introducing duct 20E of the embodiment as shown in FIG. 18 and FIG. 19. In addition, a spiral duct 24 is provided in a rotatable manner on the outer circumferential surface of the elastic cover tube 81.

The elastic cover tube 81 is formed by, for example, elongated and flexible Teflon™ resin having a small friction resistance. A first through-hole 81a, a second through-hole 81b, and a third through-hole 81c are provided in the elastic cover tube 81. A flange portion 81d is provided at the distal portion of the elastic cover tube 81.

The first through-hole 81a is a through-hole for inserting the insertion portion 11 of the endoscope 2. Accordingly, a closing window member 57 for sealing the distal side aperture of the first through-hole 81a is fixed at the distal surface of the flange portion 81d of the elastic cover tube 81 so that a water-tight state is ensured.

The second through-hole 81b is an air and water supply channel. Accordingly, an air and water supply nozzle 83 is fixedly provided at the distal portion of the second through-hole 81b. The aperture of the air and water supply 83 is opposing the closing window member 57. Accordingly, when, for example, carrion and the like are attached to the closing window member 57, the attached carrion can be flushed away by ejecting, for example, water as shown in the arrow from the aperture of the air and water supply nozzle 83. Further, drop of water and the like attached to the surface of the closing window member 57 can be removed by, for example, ejecting air from the aperture of the air and water supply nozzle 83.

Then, the third through-hole 81c is an aspiration channel.

The spiral tube 24 is provided at the outer circumferential surface of the elastic cover tube 81 in a rotatable manner. Dropout of the spiral tube 24 is prevented by providing the flange portion 81d at the distal portion of the elastic cover tube 81. Note that the circular member 52 may also be provided at the wall surface of the distal side formed by the flange portion 81d in the embodiment.

On the other hand, the proximal portion constituting member 82 is formed by a tubular resin member and the proximal surface of the spiral duct 24 contacts at the distal surface side of the proximal portion constituting member 82. A first concave portion 82a in which the proximal portion of the elastic cover tube 81 is engageably inserted to be disposed is provided at the distal side portion of the proximal portion constituting member 82. On the other hand, a second concave portion 82b in which the distal side portion of the handling portion 12 of the endoscope 2 is provided is provided at the proximal side portion of the proximal portion constituting member 82. The first concave portion 82a and the second concave portion 82b are communicated by a through hole 82c having an inner diameter where the insertion portion 11 can pass through.

In addition, an air and water supply hole 82d which is a continuous hole communicated with the second through-hole 81b provided at the elastic cover tube 81 and a hole for aspiration (not shown) which is a continuous hole communicated with the third through-hole 81c at predetermined positions of the proximal portion constituting member 82. Duct line connecting members 84 are respectively provided at end of the air and water supply hole 82d and the aspiration hole.

An air and water supply duct line 85a extended from the air and water supply device 85 is connected with the duct line connecting member 84 provided at the hole for the air and water supply 82d. On the other hand, an aspiration duct line (not shown) extended from an aspiration device (not shown) is connected with the duct line connecting member (not shown) provided at the hole for aspiration.

The air and water supply device 85 and the aspiration device are electrically connected with, for example, the video processor 5 in the embodiment. Moreover, an air and water supply push-button switch (hereinafter, abbreviated as first switch) 87 and an aspiration push-button switch (hereinafter, abbreviated as second switch) 88 are provided at the handling portion 12 of the endoscope 2.

The first switch 87 includes a button portion 87b having a detecting portion 87a and sensors 87c and 87d for detecting the detecting portion 87a. Correspondingly, the second switch 88 includes a button portion 88b having a detecting portion 88a and sensor 88c for detecting the detecting portion 88a. Note that reference numeral 89a refers to a spring for biasing the button portions 87c and 88b to the position in the drawing. Reference numeral 89b refers to signal lines extended from each sensor 87c, 87d, and 88c and are electrically connected to the video processor 5.

Thereby, the air and water supply device 85 becomes air supply state when, for example, the button portion 87b of the first switch 87 is push operated and the position of the detecting portion 87a is detected by the sensor 87c. Then, the air and water supply device 85 is to be shifted from air supply state to water supply state when the button portion 87b is push operated and the position of the detecting portion 87a is detected by the sensors 87d. On the other hand, the aspiration device becomes aspiration state when, for example, the button portion 88b of the second switch 88 is push operated and the detecting portion 88a is detected by the sensor 88c.

In this manner, the diameter of the introducing portion can be reduced by providing only a closing window 18 constituting an observation optical system and an illumination window 19 constituting an illumination optical system at the distal surface of the insertion portion 11 in the endoscope 2A of the embodiment which is inserted to be disposed in the first through-hole 81a of the elastic cover tube 81 by providing the second through-hole 81b for air and water supply and the third through-hole 81c for aspiration at the elastic cover tube.

Figure 20:
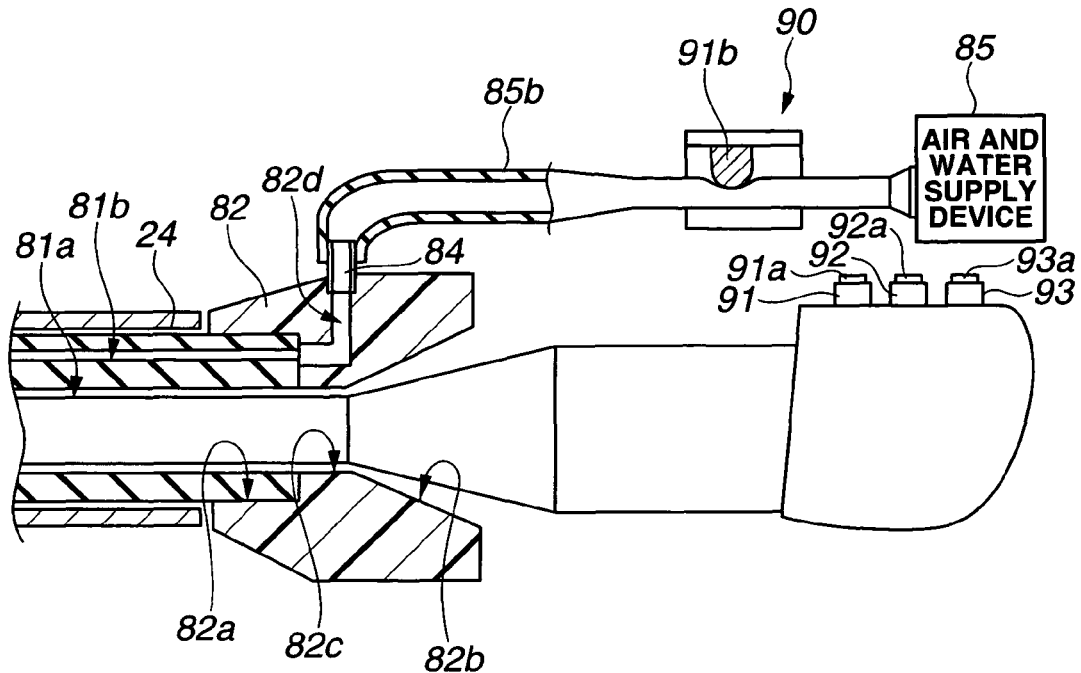
FIG. 20 is a diagram illustrating an introducing duct equipped with an electromagnetic valve for carrying out supply control of fluid.
Figure 21:
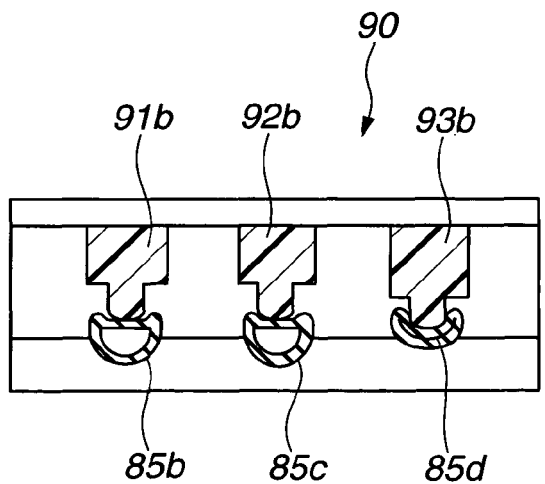
FIG. 21 is a diagram illustrating an exemplary operation of the electromagnetic valve.
Figure 22:
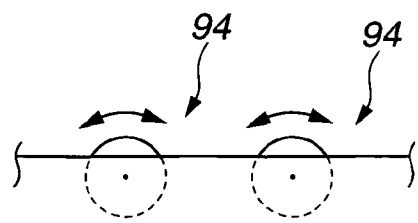
FIG. 22 a diagram illustrating another construction of switches carrying out fluid control.

Note that an electromagnetic valve 90 may be provided at a half way portion of an air supply duct line 85b and a water supply duct line 85c extended form, for example, the air and water supply device 85 and an aspiration duct line 85d extended from the aspiration device (not shown), at the same time, an air supplying touch censer 91, a water supplying touch censer 92a, and an aspirating touch censer 91a may be provided at switch portions 91, 92, and 93 provided at, for example, the handling portion 12 as shown in FIG. 20 and FIG. 21. Thereby, air supply, water supply, and aspiration can be carried out by changing the duct line corresponding to the operated touch sensor to open state. Water supply is performed by operating the water supplying touch censer 92a to shift an air supplying piston 91b and a water supplying piston 92b to open the air duct line 85b and water duct line 85c in FIG. 21.

Sensors provided at the switch portions 91, 92, and 93 are not limited to the touch censers 91a, 92a, and 93a and may be photo censers or the like. Further, the switch portions 91, 92, and 93 may be a dial switch 94 equipped with a rotatable dial as shown in the arrow in FIG. 22. In the dial switch, positions of each piston 91b, 92b, and 93b are changed in accordance with a rotation position of the dial. Accordingly, adjustment of ejecting amount and adjustment of aspiration amount may be performed during water and air supply by shifting a rotation position of the dial switch 94.

Figure 23:
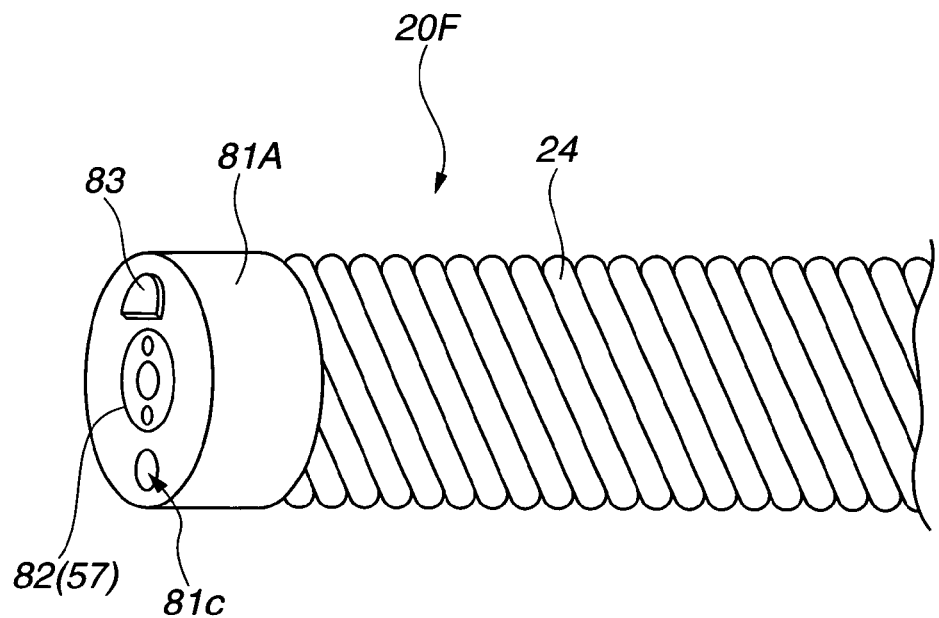
FIG. 23 is a perspective view illustrating an introducing duct in which the insertion portion of the endoscope is disposed between an air and water supply nozzle and an aperture of an aspiration channel.

In addition, a second through-hole 81b, and a third through-hole 81c may be provided to sandwich a first through-hole 81a in which the insertion portion 11 of the endoscope 2 is inserted to be provided as the introducing duct 20F shown in FIG. 23. Thereby, the balance of the flexibility of the introducing duct 20F is approximately maintained at comparable level in up and down directions as well as in left and right directions as compared to the constitution of the introducing duct 20E in which the air and water supply channel and the aspiration channel are provided at one side of the distal surface of the insertion portion 11 as shown in FIG. 18.

A construction and an operation thereof of the introducing duct having characteristics in the constitution of the spiral duct will be described with reference to FIG. 24.

Figure 24:
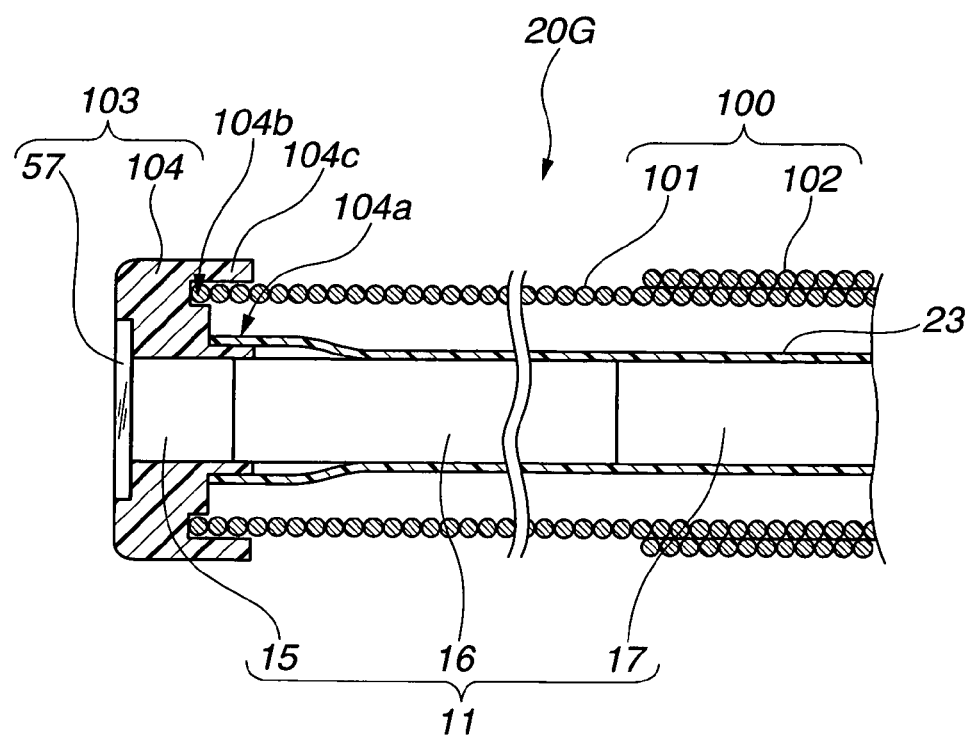
FIG. 24 is a diagram illustrating an exemplary construction of the introducing duct characterized in the construction of the spiral duct.

A constitution of the spiral duct 100 disposed at outer circumferential surface side of the cover member 23 is different from the embodiments described above for the introducing duct 20G of the embodiment as shown in FIG. 24. The spiral duct 100 includes a single layer portion 101 having good flexibility and a plural layers portion 102 having a predetermined flexibility although harder than the single layer portion 101. The single layer portion 101 is constituted by winding a single metal wire in the spiral manner and the plural layers portion 102 is constituted by winding two metal wires in the spiral manner.

Moreover, the single layer portion 101 is disposed to cover the bending section 16 of the insertion portion 11 and the vicinity thereof. Accordingly, when the bending section 16 is bent, the desired bending operation is performed without losing bending property of the bending section 16 by providing the single layer portion 101 to the bending section 16. Correspondingly, the plural layers portion 102 is disposed to cover the flexible duct portion 17 at the proximal side than the bending section 16. Therefore the rotation power of the rotating power transmission member 45 is effectively transmitted to the spiral duct 100 by disposing the rotating power transmission member 45 rotated by the motor 44 provided in the rotating mechanism portion 42 to the plural layers portion 102.

Note that the distal portion body 103 includes a tubular distal duct member 104 provided with a first shoulder 104a, a second shoulder 104b, and a retaining 104c at the proximal portion side and a closing window member 57 provided at the distal surface of the distal duct member 104 in the embodiment. Thereby, the single layer portion 101 is disposed at the second shoulder 104b with covered state by the retaining 104c provided at the distal duct member 104. Therefore the single layer portion 101 can surely be prevented from dropping off from the distal duct member 104.

Figure 25:
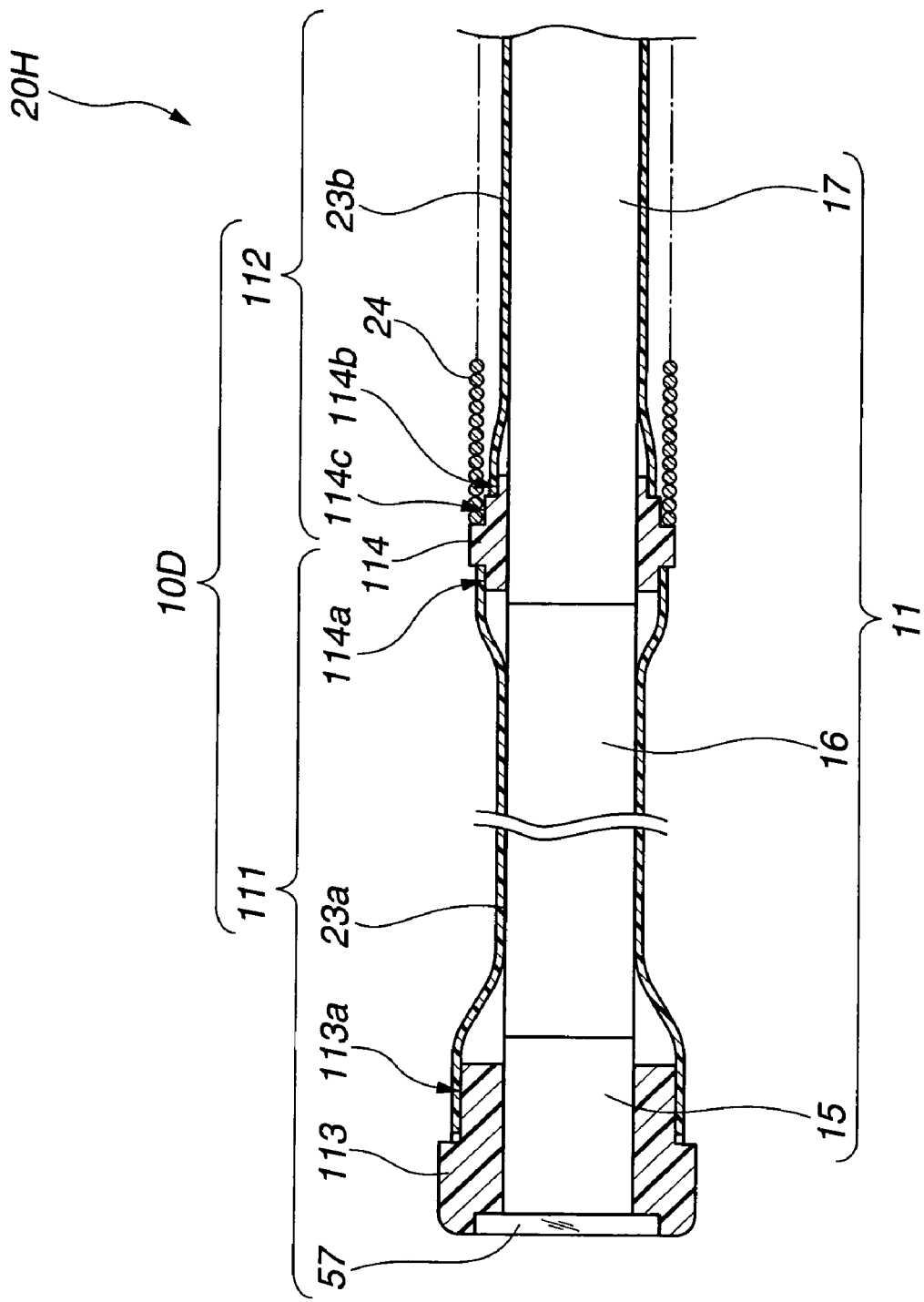
FIG. 25 is a diagram illustrating another exemplary construction of the introducing duct characterized in the construction of the spiral duct.

Another construction and operation thereof of the introducing duct having characteristics in the constitution of the spiral duct will be described with reference to FIG. 25. The insertion portion cover 10D comprises a first cover portion 111 and a second cover portion 112 for the introducing duct 20H of the embodiment as shown in FIG. 20. The first cover portion 111 covers the bending section 16 and the vicinity thereof of the insertion portion 11. The second cover portion 112 covers the flexible duct portion 17 at the proximal side than the bending section 16.

The first cover portion 111 includes a tubular distal duct member 113, a closing window member 57, a tubular half way portion duct member 114, and a first cover member 23a. The distal portion body includes the distal duct member 113 and the closing window member 57. The ends of the first cover member 23a are fixed to the distal duct member 113 and the half way portion duct member 114 in a water-tight manner. Accordingly, a shoulder 113a and a shoulder 114a in which the first cover member 23a is fixed in a water-tight manner are respectively provided on the proximal portion outer circumferential surface of the distal duct member 113 and the distal portion outer circumferential surface of the half way portion duct member 114.

On the other hand, the second cover portion 112 includes a half way portion duct member 114, a proximal portion body 51 not shown, and a second cover member 23b. The ends of the second cover member 23b are fixed to the half way portion duct member 114 and the proximal portion body 51 in a water-tight manner. Moreover, a spiral duct 24 is to be formed at the outer circumferential side of the second cover member 23b. A first shoulder 114b and a second shoulder 114c are provided on the proximal portion outer circumferential surface of the half way portion duct member 114. The second cover member 23b is fixed at the first shoulder 114b in a water-tight manner. The spiral duct 24 is provided in a rotatable manner at the second shoulder 114c.

Note that the half way portion duct member 114 is to be integrally provided at the distal side portion of the flexible duct portion 17 by, for example, elastic force. Thereby, the bending section 16 covered with the first cover portion 111 is bent without losing bending property.

A construction and operation of still another construction of the introducing duct having an insertion portion cover will be described with reference to from FIG. 26 to FIG. 29.

Figure 26:
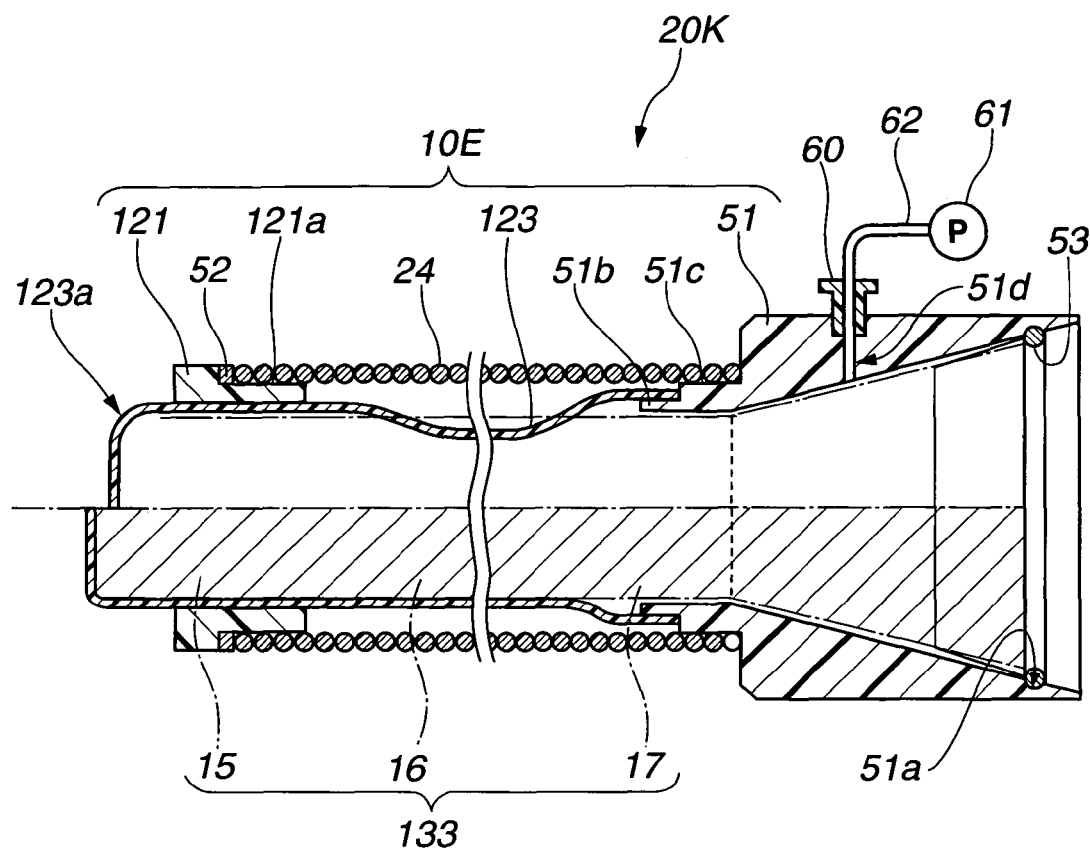
FIG. 26 is a diagram illustrating another construction of the introducing duct.

An insertion portion cover 10E which is insertion portion covering means includes a distal portion body 121, a proximal portion body 51, and a cover member 123 for the introducing duct 20K of the embodiment as shown in FIG. 26. The spiral duct 24 is disposed in a rotatable manner with respect to the distal portion body 121 and the proximal portion body 51. In addition, a circular member 52 is fixedly provided at a predetermined position of the distal portion body 121.

The cover member 123 is an elongated and thin-walled elastic member having optical transparency and one end is constituted as a pouched portion 123a and another end is constituted as an aperture.

The distal portion body 121 is tubular and formed by a resin member. A shoulder 121a in which the spiral duct 24 is disposed in a rotatable manner is formed on the proximal portion side outer circumferential surface of the cover member 123. A predetermined position of the cover member 123 is integrally adherently fixed by, for example, adhesion on the inner circumferential surface of the distal portion body 121. Thereby, the pouched portion 123a of the cover member 123 projects a predetermined amount from the distal surface of the distal portion body 121. The distal portion aperture of the cover member 123 is fixed to the first shoulder portion 51b of the proximal portion body 51 in a water-tight manner by, for example, adhesion.

Each ends of the spiral duct 24 are disposed at the shoulder 121a of the distal portion body 21 and the second shoulder 51c of the proximal portion body 51 in a rotatable manner. The circular member 52 is integrally fixedly provided to a wall face formed at the shoulder 121a of the distal portion body 121 by, for example, adhesion. The other construction is the same as the embodiment describe above, so that the same reference numeral is applied to the same member to skip the description.

Figure 27:
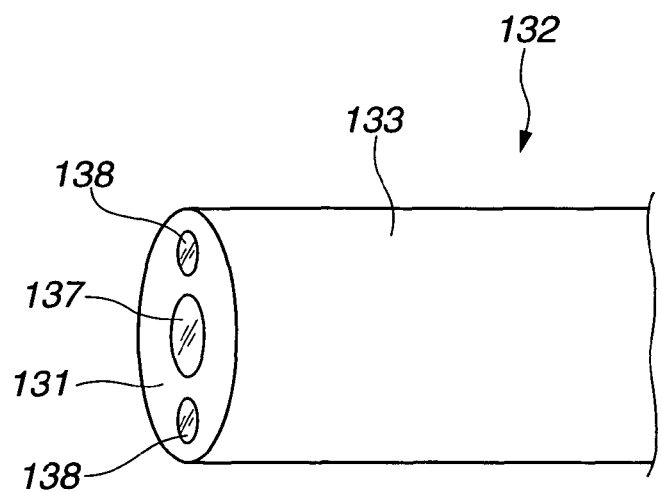
FIG. 27 is a diagram illustrating an exemplary construction of an insertion portion distal portion of the endoscope provided in the introducing duct shown in FIG. 26.
Figure 28:
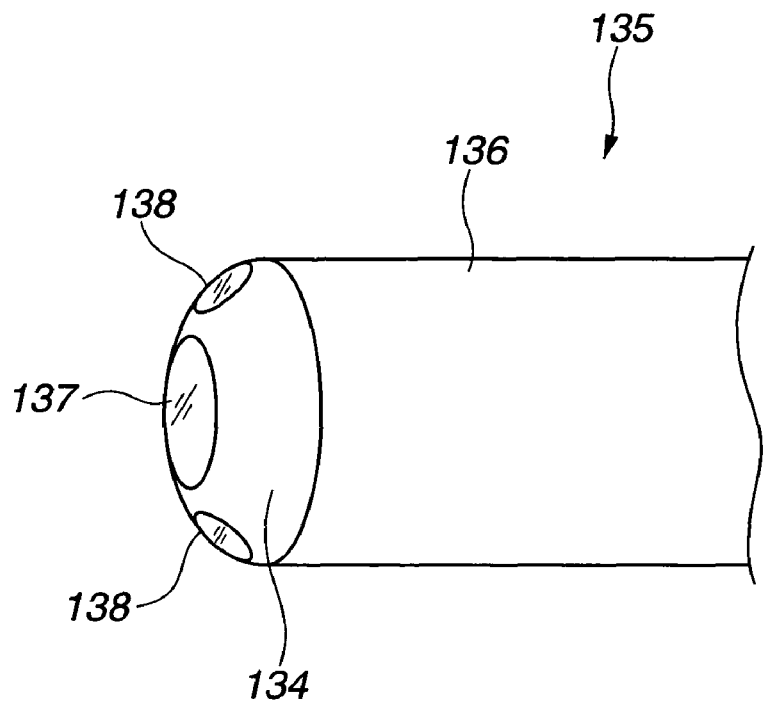
FIG. 28 is a diagram illustrating another exemplary construction of the insertion portion distal portion of the endoscope disposed in the introducing duct shown in FIG. 26.

Accordingly, when the insertion portion 133 of the endoscope 132 in which the distal surface 131 is constituted by a plane surface as shown in FIG. 27 or the insertion portion 136 of the endoscope 135 in which the distal surface 134 is constituted by, for example, a curved surface as shown in FIG. 28 is inserted into the insertion portion cover 10E of the introducing duct 20K of the embodiment, the pouched portion 123a is deformed to be adherently disposed so as to fit with the distal surface shape. Reference numeral 137 refers to a lens for observation and reference numeral 138 refers to a lens for illumination.

In this manner, the cover member constituting the insertion portion cover provided at the introducing duct is formed by the elastic member and the pouched portion is provided at one end portion. Then, the distal portion of the insertion portion is covered to be disposed at the pouched portion. Thereby, the thin-walled insertion portion cover can be adherently disposed at the distal portion of the insertion portion regardless of the insertion portion distal shape of the endoscope inserted to be disposed in the insertion portion cover. The other operation and effect are the same as in the embodiment described above.

Note that a stopping groove (not shown) may be formed at the distal portion of the endoscope 132 (not shown) and the distal side portion of the handling portion (not shown) as displacement preventing means for preventing displacement of the proximal portion body 51 in the circumferential direction. Convex portions engageably inserted to be disposed at the stopping groove are respectively provided at the insertion portion body and the distal portion body when forming the stopping groove.

Figure 29:
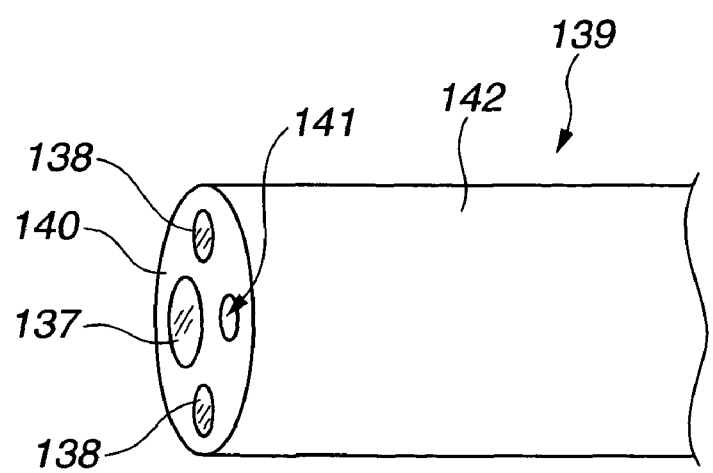
FIG. 29 is a diagram illustrating an insertion portion having an aperture of the insertion duct line disposed in the introducing duct shown in FIG. 26.

In the case where the aperture 141 which doubles an aspiration duct and a treatment device insertion channel is included on the distal surface 140 of the endoscope 139 as shown in FIG. 29, the aperture 141 is operated as an aspiration duct in the state where the insertion portion 142 is disposed in the insertion portion cover 10E. Thereby, the pouched portion 123a of the insertion portion cover 42 can be surely adhered to the distal surface 140 to surely prevent displacement and the like of the insertion portion cover 123 under inspection.

Note that the present invention is not limited to only the embodiments described above and various different embodiments may be available without departing from the gist of the present invention.

What is claimed is:

1. An insertion apparatus, comprising:
    an introducing duct, including:
        an insertion portion cover portion for covering in a water-tight manner from an end surface of an insertion portion extending from a distal side portion of a handling portion constituting an endoscope to a crack stop constituting the distal end side of the handling portion, the insertion portion including a closing window portion at an end surface thereof for performing endoscopy of an examinee's body, the insertion portion cover portion being adapted to rotate around an axis of the insertion portion; and
        a spiral duct integrally fixed on an outer circumferential surface side of the insertion portion cover portion, the spiral duct having, on a circumferential surface of the spiral duct, a propulsion power generating portion which is rotated to cause an outer surface thereof to contact a part to be examined, for applying a propulsion power for introducing the insertion portion covered by the insertion portion cover portion into a deep portion in a body cavity; and
    a rotating device comprising a rotating portion for rotating the introducing duct,
    wherein the insertion portion cover portion comprises:
        a distal portion body, having a cylindrical shape, comprising a closing window portion and an aperture side in which one end of the spiral duct is placed, the distal portion body being disposed to cover a distal portion constituting the insertion portion;
        a proximal portion body having a cylindrical shape and in which another end of the spiral duct is disposed, the proximal portion body being disposed at the distal side portion of the handling portion; and
        a flexible tubular cover member made of resin whose ends are disposed in a water-tight manner with respect to the distal portion body and the proximal portion body.

2. The insertion apparatus according to claim 1, wherein, in a constitution in which the spiral duct is fixed to the distal portion body and the proximal portion body,
    an inner circumferential surface of the proximal portion body is provided with a stop convex portion, and an outer circumferential surface of the distal side portion of the handling portion is provided with a circumferential groove in which the stop convex portion is freely disposed, and a stopping groove in which the stop convex portion is engageably inserted.

3. The insertion apparatus according to claim 2, wherein at least one of a member constituting the proximal portion body and a member constituting the distal side portion of the handling portion is a member having a good tribological property.

4. The insertion apparatus according to claim 2, wherein the circumferential groove is positioned toward the insertion portion by a predetermined interval in a longitudinal axial direction from the stopping groove.

5. The insertion apparatus according to claim 2, wherein a forming position of the stopping groove is set at a position such that a distal surface of the distal portion is disposed contactingly to a surface of the closing window portion of the distal portion body of the insertion portion cover portion, in a state where the stop convex portion is inserted in the stopping groove.

6. The insertion apparatus according to claim 4, wherein an inclined surface for guiding the stop convex portion from the circumferential groove to the stopping groove is provided between the circumferential groove and the stopping groove which are formed in this order from the insertion portion side in the longitudinal axial direction.

7. The insertion apparatus according to claim 1, wherein, in a constitution in which the spiral duct is rotatably disposed with respect to the distal portion body and the proximal portion body, at least one of the distal portion body and the proximal portion body is provided with a fixing portion for integrally disposing the distal portion body to the distal portion constituting the insertion portion, or for integrally disposing the proximal portion body to the distal side portion of the handling portion.

8. The insertion apparatus according to claim 7, wherein, in a constitution in which the spiral duct is rotatably disposed with respect to the distal portion body and the proximal portion body, the distal portion body is provided with a circular member formed of a rigid member to which an end surface of the spiral duct contacts.

9. The insertion apparatus according to claim 7, wherein the fixing portion is an O ring provided to the distal portion body or the proximal portion body.

10. The insertion apparatus according to claim 7, wherein the fixing portion is an elastic member forming the distal portion body.

11. The insertion apparatus according to claim 7, wherein the fixing portion is a convex portion provided on an inner circumferential surface of the distal portion body or the proximal portion body, and is a concave portion provided to the insertion portion in a corresponding manner to the convex portion.

12. The insertion apparatus according to claim 7, wherein the proximal portion body is provided with a continuous hole communicating an inner circumferential surface side and an outer circumferential surface side of the proximal portion body.

13. The insertion apparatus according to claim 1, wherein the distal portion body is configured by a tubular distal duct member having a tubular shape, and the closing window portion of the distal portion body has an optical property and is disposed on a distal surface of the tubular distal duct member.

14. The insertion apparatus according to claim 7, wherein a distal portion of the insertion portion or the distal side portion of the handling portion is provided with a displacement preventing groove for preventing displacement of the distal portion body or the proximal portion body in the circumferential direction.

15. An insertion apparatus comprising:
an endoscope comprising:
a handling portion; and
an insertion portion, extending from a distal side of the handling portion, configured to be inserted within a cavity; and
an introducing duct comprising:
an insertion portion cover portion configured to cover the insertion portion of the endoscope;
a propulsion power generation portion, arranged on an outer circumferential surface side of the insertion portion cover portion, configured to convert a rotation power applied to the insertion power cover portion to a propulsion power to propel against the inner surface of the cavity in a longitudinal axial direction of the insertion portion cover portion; and
a propulsion power transmission portion, arranged on an inner circumferential surface side of the insertion portion cover portion, configured to transmit the propulsion power generated by the propulsion power generating portion to the endoscope;
wherein the handling portion of the endoscope comprises:
a circumferential groove configured to receive the propulsion power transmission portion such that the propulsion power transmission portion can be rotationally moved along the circumferential groove; and
a stop groove configured to receive the propulsion power transmission portion and to limit rotational movement of the propulsion power transmission portion relative to the handling portion of the endoscope.

16. The insertion apparatus according to claim 15, wherein the insertion portion cover portion comprises:
a distal portion body having a substantially cylindrical shape, the distal portion body comprising a closing window portion and an aperture side to which a distal end of the propulsion power generation portion is arranged, the distal portion body being disposed to cover a distal portion of the insertion portion of the endoscope;
a proximal portion body, having a substantially cylindrical shape, to which a proximal end of the propulsion power generation portion is arranged; and
a flexible cover member having a first end operatively connected in a water-tight manner with the distal portion body and a second end operatively connected in a water-tight manner with the proximal portion body.

17. The insertion apparatus according to claim 16, wherein the propulsion power transmission portion is arranged to an inner circumferential surface of the proximal portion body of the insertion portion cover portion.

18. The insertion apparatus according to claim 17, wherein at least one of a portion of the inner circumferential surface of the proximal portion body and a portion of the handling portion which comes in contact with the portion of the inner circumferential surface of the proximal portion body has a tribological property to facilitate relative movement of the endoscope and the introducing duct.

19. The insertion apparatus according to claim 15, wherein the circumferential groove of the endoscope is positioned toward the insertion portion of the endoscope by a predetermined interval in a longitudinal axial direction from the stop groove.

20. The insertion apparatus according to claim 17, wherein a forming position of the stop groove is set at a position such that a distal surface of the insertion portion of the endoscope is disposed contactingly to a surface of the closing window portion, in a state where the propulsion power transmission portion is inserted in the stop groove.

21. The insertion apparatus according to claim 19, the handling portion of the endoscope further comprises an inclined surface, provided between the circumferential groove and the stop groove, for guiding the propulsion power transmission portion from the circumferential groove to the stop groove.

* * * * *